(12) United States Patent
Bovin et al.

(10) Patent No.: US 10,408,717 B2
(45) Date of Patent: Sep. 10, 2019

(54) PRINTING OF FSL CONSTRUCTS

(71) Applicants: Nicolai Vladimirovich Bovin, Moscow (RU); Stephen Micheal Henry, Auckland (NZ); Stephen Robert Parker, Auckland (NZ)

(72) Inventors: Nicolai Vladimirovich Bovin, Moscow (RU); Stephen Micheal Henry, Auckland (NZ); Stephen Robert Parker, Auckland (NZ)

( * ) Notice: Subject to any disclaimer, the term of this patent is extended or adjusted under 35 U.S.C. 154(b) by 0 days.

(21) Appl. No.: 15/954,295

(22) Filed: Apr. 16, 2018

(65) Prior Publication Data

US 2019/0003938 A1 Jan. 3, 2019

Related U.S. Application Data

(63) Continuation-in-part of application No. 13/380,711, filed as application No. PCT/NZ2010/000127 on Jun. 29, 2010, now Pat. No. 9,970,928.

(30) Foreign Application Priority Data

| Jun. 29, 2009 | (NZ) | 578036 |
| Jul. 10, 2009 | (NZ) | 578338 |
| Nov. 26, 2009 | (NZ) | 581481 |
| Feb. 23, 2010 | (NZ) | 583516 |
| Jun. 25, 2010 | (NZ) | 586448 |

(51) Int. Cl.
| *G01N 1/40* | (2006.01) |
| *G01N 33/92* | (2006.01) |
| *G01N 33/53* | (2006.01) |

(52) U.S. Cl.
CPC ........ *G01N 1/4077* (2013.01); *G01N 33/5308* (2013.01); *G01N 33/92* (2013.01)

(58) Field of Classification Search
None
See application file for complete search history.

(56) References Cited

FOREIGN PATENT DOCUMENTS

| CN | 1952658 | 4/2007 |
| JP | 2000-144025 | 5/2000 |
| WO | WO 2004/108743 | 12/2004 |
| WO | WO 2005/090368 | 9/2005 |
| WO | WO 2007/035116 | 3/2007 |
| WO | WO 2009/035347 | 3/2009 |
| WO | WO 2009/048343 | 4/2009 |
| WO | WO 2010/039049 | 4/2010 |

OTHER PUBLICATIONS

Liberski, Albert, et al; "Inkjet fabrication of polymer microarrays and grids-solving the evaporation problem"; *Chemical Communications*, pp. 334-336 (2009) XP008150234 (D2).
Supplementary European Search Report, issued in European Patent Application No. 10794415.9 dated Oct. 15, 2013 (6 pgs).
International Search Report for PCT/NZ2010/000127 dated Oct. 13, 2010.
Barbulovic-Nad et al; "Bio-Microarray Fabrication Techniques—A Review"; *Critical Reviews in Biotechnology*, vol. 26, pp. 237-259 (2006).
Fukui, S., et al; "Oligosaccharide microarrays for high-throughput detection and specificity assignments of carbohydrate-protein interactions"; *Nature Biotechnology*, vol. 20, pp. 1011-1017 (2002).
O Blixt et al., "Printed covalent glycan array for ligand profiling of diverse glycan binding proteins", PNAS 2004 101, pp. 17033-17038.

*Primary Examiner* — Christopher M Gross
(74) *Attorney, Agent, or Firm* — Nixon & Vanderhye P.C.

(57) ABSTRACT

Method of localizing cells to at least one discrete area on a surface of a substrate by propelling droplets of an aqueous dispersion of a synthetic construct of the structure F-S-L from a plurality of orifices located in a print head of an inkjet printer onto the surface. In the structure F-S-L, F is a functional moiety capable of associating with the cells by dire

FIGURE 2

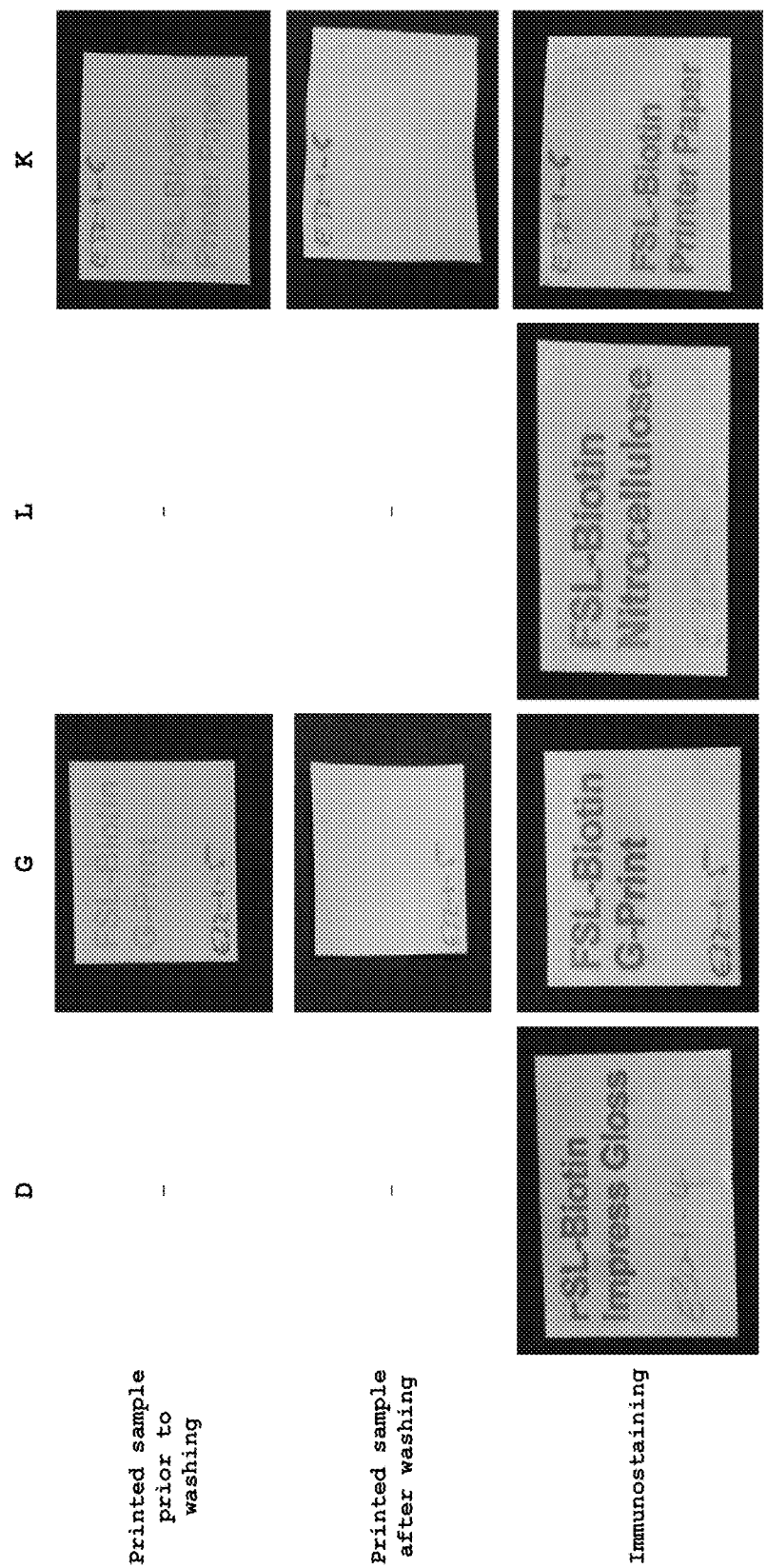

PRINTING OF FSL CONSTRUCTS

This application is a continuation-in-part of Ser. No. 13/380,711 filed Mar. 16, 2012, now U.S. Pat. No. 9,970,928, which is the U.S. national phase of International Application No. PCT/NZ2010/000127 filed Jun. 29, 2010, which designated the U.S. and claims priority to NZ Patent Application No. 586448 filed Jun. 25, 2010, No. 583516 filed Feb. 23, 2010, No. 581481 filed Nov. 26, 2009, No. 578338 filed Jul. 10, 2009, and No. 578036 filed Jun. 29, 2009, the entire contents of each of which are hereby incorporated by reference.

FIELD OF INVENTION

The invention relates to a method of printing constructs of the generic structure F-S-L (where F is a functional moiety, S is a spacer covalently linking F to L, and L is a lipid). In particular, the invention relates to the use of the method in the fabrication of diagnostic test cards and sticks, microarrays and multiwell plates and the localisation of cells to discrete areas.

BACKGROUND ART

Glycomics has emerged with proteomics as an area for development and exploration in the postgenomics era (Blixt et al (2004)). Despite the increasing awareness of the biological significance of carbohydrates, the study of carbohydrate-protein interactions still encounters much difficulty. There is a need for the development of highly sensitive and high-throughput methods for identification and binding study of carbohydrates recognized by various receptors (Chung-Yi et al (2009)).

The immobilization of glycans on the derivatised surface of substrates is a commonly employed method of fabricating glycan microarrays. Blixt et al (2004) discloses immobilisation of amine functionalised synthetic glycan ligands on N-hydroxysuccinimide (NHS) activated glass slides using a custom made robotic printing arrayer. Bovin and Huflejt (2008) have reviewed the use of binding chemistries exploiting amide bond formation. Short spacers are used to reduce non-specific contacts to a minimum. Attachment to a flexible layer of polyethylene glycol on a glass surface is presented as assuring availability of glycan moieties for interaction with binding molecules.

The localization of glycans to the surface of substrates in the form of neoglycolipids has also been employed as a method of fabricating glycan microarrays. Chai et al (2003) describe a multiwell-binding assay in which neoglycolipids are diluted either in methanol, or in methanol containing the carrier lipids egg lecithin and cholesterol. The dispersions of neoglycolipids are then used to coat the wells of the multiwell plates. Chai et al (2004) describe the bandwise application of the dispersions of neoglycolipids by a spray-on technique employing a sample applicator comprising a single syringe as applicator (LINOMAT IV, Camag, Switzerland)

Fukui et al (2005) and Huang et al (2006a, 2006b) have each described a non-covalent glycoarray assembly method utilising lipid-linked saccharides and oligosaccharides. Both methods employ reductive amination to produce a lipid-linked saccharide of oligosaccharide (neoglycolipid). In the method of Fukui et al (2005) oligosaccharides were conjugated to 1,2-dihexadecyl-sn-glycero-3-phosphoethanolamine (DHPE) directly or after mild periodate oxidation. The neoglycolipids were then applied by jet spray as bands or spots onto nitrocellulose membranes. In the method of Huang et al (2006a, 2006b) the reaction to produce lipid-linked saccharides uses an excess of saccharides in order to exhaust the tetradecylamine employed in the reaction. The lipid-linked saccharides were then applied to multi-well high binding polystyrene plates.

Liu et al (2006) describe the preparation of neoglycolipids from N-aminooxyacetal DHPE (AOPE) by a chemoselective oxime-ligation reaction with reducing sugars. The binding of the neoglycolipids by antibodies and lectins was assayed by an enzyme-linked immunosorbent assay (ELISA) in plastic microwells as described by Chai et al (2003). In these studies the neoglycolipids were incorporated into liposomes for arraying and spotted onto nitrocellulose membranes or robotically arrayed onto nitrocellulose-coated glass slides.

Palma et al (2006) and Campanero-Rhodes et al (2007) describe the preparation of arrays of natural and synthetic glycolipids and neoglycoplipids by printing on nitrocellulose-coated glass slides using a non-contact piezoelectric arrayer (PIEZORRAY, Perkin-Elmer, United Kingdom). Liu et al (2007) also describes the use of this non-contact piezoelectric arrayer. The arrayer employs an assembly containing four PIEZOTIP™ dispensers to dispense sub-nanoliter to nanoliter volumes with 20 to 25 μm accuracy and precision.

Barbulovic-Nad et al (2006) reviews techniques for the fabrication of bio-microarrays. The challenges of applying inkjet technologies to the fabrication of bio-microarrays are identified.

It is an object of the invention to provide an improved method for the localisation of functional moieties, including glycans, to the surface of substrates.

It is an object of the invention to provide a method of fabricating diagnostic test cards and sticks, microarrays and multiwell plates.

It is an object of the invention to provide templates for use in the fabrication of diagnostic test cards and sticks, microarrays and multiwell plates microarray formats by the method that improve accuracy and reliability of assay results.

It is an object of the invention to provide a method of localizing cells to discrete areas on the surface of a substrate.

These objects are each to be read disjunctively with the object to at least provide the public with a useful choice.

STATEMENT OF INVENTION

In a first aspect the invention provides a method of localising a functional moiety (F) to at least one discrete area on a surface of a substrate including the step of propelling droplets of a dispersion of a synthetic construct of the structure F-S-L from a plurality of orifices located in a monolithic print head onto the surface of the substrate where:

S is a spacer (S) selected to provide a construct that is dispersible in water in the absence of organic solvents or detergents at a temperature of 25° C.; and L is a diacyl- or dialkyl lipid.

Preferably, F is biotin, a glycan or a peptide.

In a first preferment of the first aspect of the invention, the at least one discrete area is in the shape of a symbol. More preferably, the at least one discrete area is in the shape of a symbol readable by optical character recognition (OCR) apparatus. Most preferably, the at least one discrete area is in the shape of a symbol comprising one or more alphanumeric characters. In a second preferment of the first aspect of the invention, the at least one discrete area is a pattern comprising a combination of indicia in which the dispersion of a synthetic construct is present at different densities (amount per unit area). The first and second preferments of this aspect of the invention are not mutually exclusive.

Preferably, the substrate is selected from the group consisting of: derivatised silica gel (e.g. $C_8$ or $C_{18}$), nitrocellulose, coated paper, silica gel or uncoated paper. More preferably, the substrate is selected from the group consisting of: coated paper or uncoated paper.

The method is a non-impact method of printing. The propelling droplets from a plurality of orifices is from a plurality of orifices located in a monolithic print head. Preferably, the propelling droplets from a plurality of orifices is from a plurality of orifices located in a monolithic print head of an inkjet printer. Most preferably, the propelling droplets from a plurality of orifices is from a plurality of orifices located in a monolithic print head of a piezoelectric inkjet printer.

Preferably, the volume of each of the droplets is 1 to 100 picoliters (pL). More preferably, the volume of each of the droplets is 1 to 50 pL. Most preferably, the volume of each of the droplets is 1 to 5 pL.

Preferably, the concentration of the synthetic construct in the dispersion is 1 μmolar (μM) to 10 mmolar (mM). More preferably, the concentration of the synthetic construct in the dispersion is 10 μM to 10 mM. Most preferably, the concentration of the synthetic construct in the dispersion is 0.1 to 10 mM.

Preferably, the synthetic construct of the structure F-S-L is dispersible in water in the absence of organic solvents or detergents at a temperature of 25° C. at a concentration of at least 6 millimolar (mM). More preferably, the synthetic construct of the structure F-S-L is dispersible in water in the absence of organic solvents or detergents at a temperature of 25° C. at a concentration of at least 12 millimolar (mM).

Preferably, L is a glycerophospholipid. More preferably, L is a phosphatidylethanolamine. Most preferably, L is selected from the group consisting of: 1,2-O-dioleoyl-sn-glycero-3-phosphatidylethanolamine (DOPE) and 1,2-O-distearyl-sn-glycero-3-phosphatidylethanolamine (DSPE).

In a first preferment of the first aspect of the invention F is a glycan. Preferably, F is a glycan that is an oligosaccharide. More preferably, F is a glycan that is an oligosaccharide selected from the group consisting of: GalNAcα3(Fucα2)Galβ-; Galα3(Fucα2)Galβ-; GalNα3(Fucα2)Galβ-; Fucα2Galβ-; Galβ4GlcNAcβ3(Galβ4GlcNAcβ6)Galβ-; Galβ4GlcNAcβ3-; Galβ4Glcβ-; Galβ3GlcNAcβ-; Galβ3(Fucα4)GlcNAcβ-; Fucα2Galβ3(Fucα4)GlcNAcβ-; GalNAcα3(Fucα2)Galβ3(Fucα4)GlcNAcβ-; Galα3(Fucα2)Galβ3(Fucα4)GlcNAcβ-; Galβ4(Fucα3)GlcNAcβ-; Fucα2Galβ4(Fucα3)GlcNAcβ-; NeuAcα2-3Galβ3(Fucα4)GlcNAcβ-; NeuAcα2-3Galβ4(Fucα3)GlcNAcβ-; GalNAcβ4(NeuAcα2-3)Galβ4-; Galβ3GalNAcα-; NeuAcα2-3Galβ4-; NeuAcα2-6Galβ4-; Galα4Galβ4-; GalNAcβGalα4Galβ4-; Galα4Galβ4GlcNAcβ3-; Galβ3GalNAcβGalα4-; NeuAcα2-3Galβ3GalNAcβGalα4-; Galα3Galβ-; GalNAcα3GalNAcβGalα4-; GalNAcβGalNAcβ3Galα4-; Galβ1-4GlcNAc; Galβ1-3GlcNAc; SAα2-6Galβ1-4Glc; SAα2-3Galβ1-4Glc; SAα2-6Galβ1-4GlcNAc; SAα2-3Galβ1-4GlcNAc; SAα2-3Galβ1-3GlcNAc; Galβ1-4(Fucα1-3)GlcNAc; Galβ1-3(Fucα1-3)GlcNAc; SAα2-3Galβ1-3(Fucα1-4)GlcNAc; SAα2-3Galβ1-4(Fucα1-3)GlcNAc; Galβ1-4GlcNAcβ1-4GlcNAc; Galβ1-3GlcNAcβ1-4GlcNAc; SAα2-6Galβ1-4GlcNAcβ1-4GlcNAc; SAα2-3Galβ1-4GlcNAcβ1-4GlcNAc; SAα2-3Galβ1-3GlcNAcβ1-4GlcNAc; Galβ1-4(Fucα1-3)GlcNAcβ1-4GlcNAc; Galβ1-3(Fucα1-4)GlcNAcβ1-4GlcNAc; SAα2-3Galβ1-3(Fucα1-4)GlcNAcβ1-4GlcNAc; SAα2-3Galβ1-4(Fucα1-3)GlcNAcβ1-4GlcNAc; SAα2-3Galβ1-3(Fucα1-4)GlcNAcβ1-4Gal; SAα2-3Galβ1-4(Fucα1-3)GlcNAcβ1-4Gal; SAα2-3Galβ1-4GlcNAcβ1-3Galβ1-4(Fucα1-3)GlcNAc; SAα2-6Galβ1-4GlcNAcβ1-3Galβ1-4(Fucα1-3)GlcNAc; SAα2-3Galβ1-4(Fucα1-3)GlcNAcβ1-3Galβ1-4Glc; SAα2-6Galβ1-4(Fucα1-3)GlcNAcβ1-3Galβ1-4Glc; SAα2-3Galβ1-4GlcNAcβ1-3Galβ1-4(Fucα1-3)GlcNAcβ1-3Galβ1-4Glc; SAα2-6Galβ1-4GlcNAcβ1-3Galβ1-4(Fucα1-3)GlcNAcβ1-3Galβ1-4Glc; SAα2-3Galβ1-4(Fucα1-3)GlcNAcβ1-3Galβ1-4Glc; SAα2-6Galβ1-4(Fucα1-3)GlcNAcβ1-3Galβ1-4(Fucα1-3)GlcNAcβ1-3Galβ1-4Glc; SAα2-3Galβ1-4(Fucα1-3)GlcNAcβ1-3Galβ1-4(Fucα1-3)Glc; SAα2-6Galβ1-4(Fucα1-3)GlcNAcβ1-3Galβ1-4(Fucα1-3)Glc; SAα2-3Galβ1-4GlcNAcβ1-3Galβ1-4(Fucα1-3)GlcNAcβ1-3Galβ1-4(Fucα1-3)Glc; SAα2-6Galβ1-4GlcNAcβ1-3Galβ1-4(Fucα1-3)GlcNAcβ1-3Galβ1-4(Fucα1-3)Glc; SAα2-3Galβ1-4(Fucα1-3)GlcNAcβ1-3Galβ1-4(Fucα1-3)GlcNAcβ1-3Galβ1-4(Fucα1-3)Glc; SAα2-6Galβ1-4(Fucα1-3)GlcNAcβ1-3Galβ1-4(Fucα1-3)GlcNAcβ1-3Galβ1-4(Fucα1-3)Glc; SAα2-3Galβ1-3(Fucα1-4)GlcNAc; SAα2-6Galβ1-3(Fucα1-4(GlcNAc; SAα2-3Galβ1-3GlcNAcβ1-4Galβ1-4(Fucα1-3)GlcNAc; SAα2-6Galβ1-3GlcNAcβ1-4Galβ1-4(Fucα1-3)GlcNAc; SAα2-3Galβ1-3(Fucα1-4)GlcNAcβ1-3Galβ1-4(Fucα1-3)GlcNAc; SAα2-6Galβ1-3(Fucα1-4)GlcNAcβ1-3Galβ1-4(Fucα1-3)GlcNAc; SAα2-3Galβ1-3(Fucα1-4)GlcNAcβ1-3Galβ1-4Glc; SAα2-6Galβ1-3(Fucα1-4)GlcNAcβ1-3Galβ1-4Glc; SAα2-3Galβ1-3GlcNAcβ1-4Galβ1-4(Fucα1-3)GlcNAcβ1-3Galβ1-4Glc; SAα2-6Galβ1-3GlcNAcβ1-4Galβ1-4(Fucα1-3)GlcNAcβ1-3Galβ1-4Glc; SAβ2-3Galβ1-3(Fucα1-4)GlcNAcβ1-3Galβ1-4(Fucα1-3)GlcNAcβ1-3Galβ1-4Glc; SAα2-6Galβ1-3(Fucα1-4)GlcNAcβ1-3Galβ1-4(Fucα1-3)GlcNAcβ1-3Galβ1-4Glc; SAα2-3Galβ1-3(Fucα1-4)GlcNAcβ1-3Galβ1-4(Fucα1-3)Glc; SAα2-6Galβ1-3(Fucα1-4)GlcNAcβ1-3Galβ1-4(Fucα1-3)Glc; SAα2-3Galβ1-3GlcNAcβ1-4Galβ1-4(Fucα1-3)GlcNAcβ1-3Galβ1-4(Fucα1-3)Glc; SAα2-6Galβ1-3GlcNAcβ1-4Galβ1-4(Fucα1-3)GlcNAcβ1-

3Galβ1-4(Fucα1-3)Glc; SAα2-3Galβ1-3(Fucα1-4)GlcNAcβ1-3Galβ1-4(Fucα1-3)GlcNAcβ1-3Galβ1-4(Fucα1-3)Glc; SAα2-6Galβ1-3(Fucα1-4)GlcNAcβ1-3Galβ1-4(Fucα1-3)GlcNAcβ1-3Galβ1-4(Fucα1-3)Glc; SAα2-3Galβ1-4GlcNAcβ1-3Galβ1-3(Fucα1-4)GlcNAc; SAα2-6Galβ1-4GlcNAcβ1-3Galβ1-3(Fucα1-4)GlcNAc; SAα2-3Galβ1-4(Fucα1-3)GlcNAcβ1-3Galβ1-3(Fucα1-4)GlcNAc; SAα2-6Galβ1-4(Fucα1-3)GlcNAcβ1-3Galβ1-3(Fucα1-4)GlcNAc; SAα2-3Galβ1-4GlcNAcβ1-3Galβ1-3(Fucα1-4)GlcNAcβ1-3Galβ1-4Glc; SAα2-6Galβ1-4GlcNAcβ1-3Galβ1-3(Fucα1-4)GlcNAcβ1-3Galβ1-4Glc; SAα2-3Galβ1-4(Fucα1-3)GlcNAcβ1-3Galβ1-3(Fucα1-4)GlcNAcβ1-3Galβ1-4Glc; SAα2-6Galβ1-4(Fucα1-3)GlcNAcβ1-3Galβ1-3(Fucα1-4)GlcNAcβ1-3Galβ1-4Glc; SAα2-3Galβ1-4(Fucα1-3)GlcNAcβ1-3Galβ1-3(Fucα1-4)Glc; SAα2-6Galβ1-4(Fucα1-3)GlcNAcβ1-3Galβ1-3(Fucα1-4)Glc; SAα2-3Galβ1-4GlcNAcβ1-3Galβ1-3(Fucα1-4)GlcNAcβ1-3Galβ1-4(Fucα1-3)Glc; SAα2-6Galβ1-4GlcNAcβ1-3Galβ1-3(Fucα1-4)GlcNAcβ1-3Galβ1-4(Fucα1-3)Glc; SAα2-3Galβ1-4(Fucα1-3)GlcNAcβ1-3Galβ1-3(Fucα1-4)GlcNAcβ1-3Galβ1-4(Fucα1-3)Glc; and SAα2-6Galβ1-4(Fucα1-3)GlcNAcβ1-3Galβ1-3(Fucα1-4)GlcNAcβ1-3Galβ1-4(Fucα1-3)Glc, where SA is sialic acid.

In a second preferment of the first aspect of the invention F is a peptide. More preferably, F is a peptide that is an oligopeptide. Most preferably, F is a peptide selected from the group listed in the Table of Peptides.

In a third preferment of the first aspect of the invention F is a conjugator. More preferably, F is a conjugator that is biotin. When F is a conjugator that is biotin, the biotin may or may not be conjugated to an avidinylated functional moiety.

Preferably, the method includes the step of coating the surface of the substrate with a polymer after the propelling of the droplets of the dispersion of the synthetic construct of the structure F-S-L onto the surface of the substrate. More preferably, the method includes the step of coating the surface of the substrate with isobutyl methacrylate polymer after the propelling of the droplets of the dispersion of the synthetic construct of the structure F-S-L.

Preferably, when F is a glycan, S is selected from the group consisting of:

where:

a and b are independently the integer 3, 4 or 5; and $R_1$ and $R_2$ are, respectively, 0 of the glycan and N of the primary amino of a diacyl or dialkyl-glycerophospholipid or N of the primary amino of a diacyl or dialkyl-glycerophospholipid and O of the glycan, or where:

M is $CH_3$ or H;

c is the integer 3, 4 or 5;

d and e are independently the integer 1, 2 or 4;

f is the integer 2, 3 or 4;

$R_3$ is N of the primary amino of a diacyl or dialkyl-glycerophospholipid; and $R_4$ is O of the glycan.

Preferably, when F is a peptide, S is selected from the group consisting of:

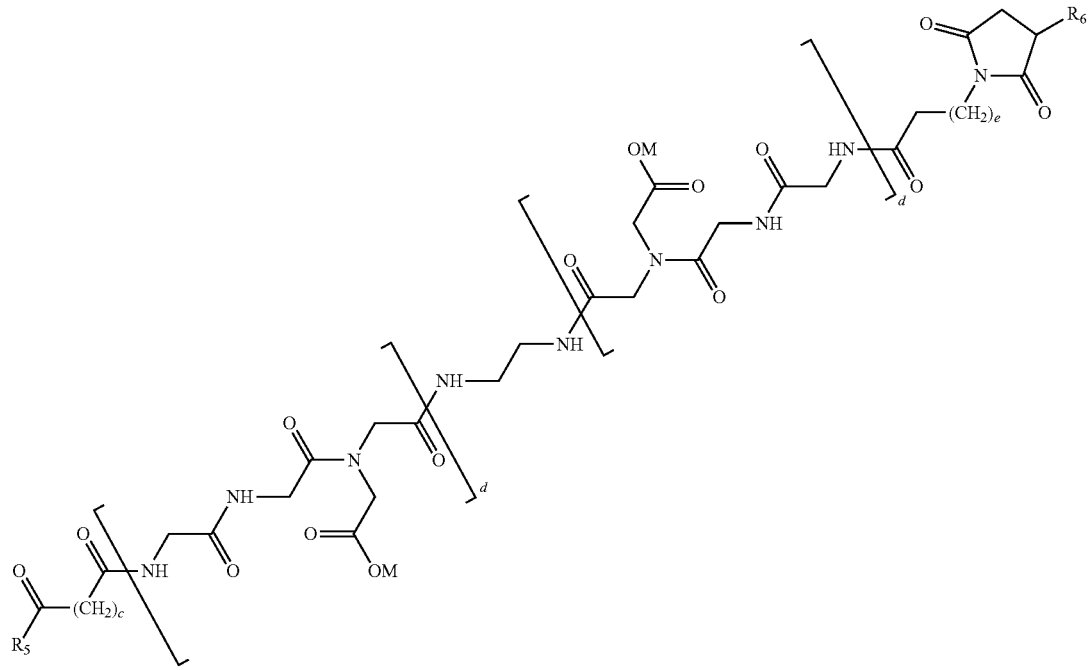

where:

M is CH₃ or H;

c is the integer 3, 4 or 5;

d and e are independently the integer 1, 2 or 4;

R₅ is N of the primary amino of a diacyl or dialkyl-glycerophospholipid; and

R₆ is S of the sulfhydryl of an amino acid residue of the peptide,

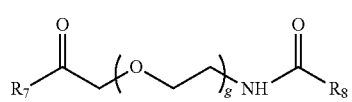

where:

g is a value in the range 6 to 14;

R₇ and R₈ are, respectively, N of the amino terminus of the peptide and N of the primary amino of a diacyl or dialkyl-glycerophospholipid or N of the primary amino of a diacyl or dialkyl-glycerophospholipid and N of the amino terminus of the peptide,

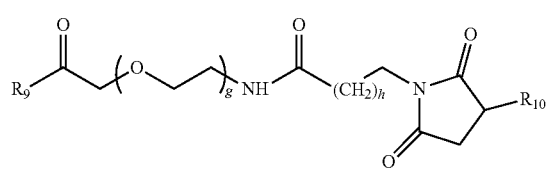

where:

g is a value in the range 6 to 14;

h is the integer 1 or 2;

R₉ is N of the primary amino of a diacyl or dialkyl-glycerophospholipid; and

R₁₀ is S of the sulfhydryl of an amino acid residue of the peptide, or

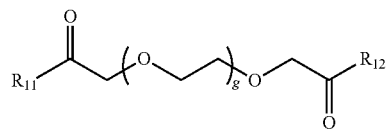

where:

g is a value in the range 6 to 14;

R₁₁ and R₁₂ are, respectively, N of the amino terminus of the peptide and N of the primary amino of a diacyl or dialkyl-glycerophospholipid or N of the primary amino of a diacyl or dialkyl-glycerophospholipid and N of the amino terminus of the peptide.

Preferably, when F is a conjugator that is biotin, F—S is selected from the group consisting of:

L is a diacyl- or dialkyl-lipid.
Preferably, F is biotin, a glycan or a peptide.

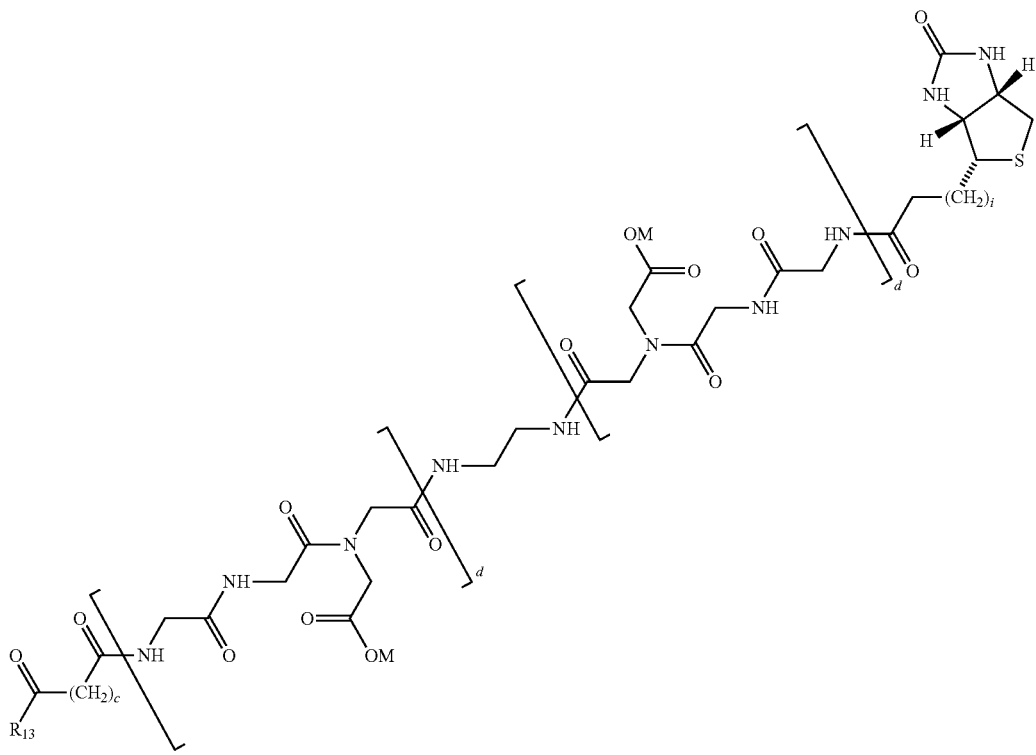

where:
M is $CH_3$ or H;
c is the integer 3, 4 or 5;
d and e are independently the integer 1, 2 or 4; and
$R_{13}$ is N of the primary amino of a diacyl or dialkyl-glycerophospholipid.

F may or may not include an avidinylated functional moiety.

In a second aspect the invention provides a diagnostic test card or stick, microarray or multiwell plate fabricated using the method of the first aspect of the invention.

In a third aspect the invention provides a method of localizing cells to at least one discrete area on a surface comprising the steps of:

Propelling droplets of a dispersion of a synthetic construct of the structure F-S-L from a plurality of orifices located in a monolithic print head onto the surface of the substrate; and then Contacting the surface with a suspension of the cells, where:

F is a functional moiety capable of associating with the cells by direct or indirect non-covalent interactions with an epitope of an antigen or biotin presented at the surface of the cells;

S is a spacer selected to provide a construct that is dispersible in water in the absence of organic solvents or detergents at a temperature of 25° C.; and Preferably, the concentration of the synthetic construct in the dispersion is 1 μmolar (μM) to 10 mmolar (mM). More preferably, the concentration of the synthetic construct in the dispersion is 10 μM to 10 mM. Most preferably, the concentration of the synthetic construct in the dispersion is 0.1 to 10 mM.

Preferably, the synthetic construct of the structure F-S-L is dispersible in water in the absence of organic solvents or detergents at a temperature of 25° C. at a concentration of at least 6 millimolar (mM). More preferably, the synthetic construct of the structure F-S-L is dispersible in water in the absence of organic solvents or detergents at a temperature of 25° C. at a concentration of at least 12 millimolar (mM).

Preferably, L is a glycerophospholipid. More preferably, L is a phosphatidylethanolamine. Most preferably, L is selected from the group consisting of: 1,2-O-dioleoyl-sn-glycero-3-phosphatidylethanolamine (DOPE) and 1,2-O-distearyl-sn-glycero-3-phosphatidylethanolamine (DSPE).

In a first preferment of the third aspect of the invention F and the epitope of the antigen are both a glycan. Preferably, the glycan is an oligosaccharide. More preferably, the oligosaccharide is selected from the group consisting of: GalNAcα3(Fucα2)Galβ-; Galα3(Fucα2)Galβ-; GalNα3(Fucα2)Galβ-; Fucα2Galβ-; Galβ4GlcNAcβ3(Galβ4GlcNAcβ6)Galβ-; Galβ4GlcNAcβ3-; Galβ4Glcβ-; Galβ3GlcNAcβ-; Galβ3(Fucα4)GlcNAcβ-; Fucα2Galβ3(Fucα4)GlcNAcβ-; GalNAcα3(Fucα2)Galβ3(Fucα4)

GlcNAcβ-; Galα3(Fucα2)Galβ3(Fucα4)GlcNAcβ-; Galβ4(Fucα3)GlcNAcβ-; Fucα2Galβ4(Fucα3)GlcNAcβ-; NeuAcα2-3Galβ3(Fucα4)GlcNAcβ-; NeuAcα2-3Galβ4(Fucα3)GlcNAcβ-; GalNAcβ4(NeuAcα2-3)Galβ4-; Galβ3GalNAcα-; NeuAcα2-3Galβ4-; NeuAcα2-6Galβ4-; Galα4Galβ4-; GalNAcβGalα4Galβ4-; Galα4Galβ4GlcNAcβ3-; Galβ3GalNAcβGalα4-; NeuAcα2-3Galβ3GalNAcβGalα4-; Galα3Galβ-; GalNAcα3GalNAcβGalα4-; GalNAcβGalNAcβ3Galα4-; Galβ1-4GlcNAc; Galβ1-3GlcNAc; SAα2-6Galβ1-4Glc; SAα2-3Galβ1-4Glc; SAα2-6Galβ1-4GlcNAc; SAα2-3Galβ1-4GlcNAc; SAα2-3Galβ1-3GlcNAc; Galβ1-4(Fucα1-3)GlcNAc; Galβ1-3(Fucα1-3)GlcNAc; SAα2-3Galβ1-3(Fucα1-4)GlcNAc; SAα2-3Galβ1-4(Fucα1-3)GlcNAc; Galβ1-4GlcNAcβ1-4GlcNAc; Galβ1-3GlcNAcβ1-4GlcNAc; SAα2-6Galβ1-4GlcNAcβ1-4GlcNAc; SAα2-3Galβ1-4GlcNAcβ1-4GlcNAc; SAα2-3Galβ1-3GlcNAcβ1-4GlcNAc; Galβ1-4(Fucα1-3)GlcNAcβ1-4GlcNAc; Galβ1-3(Fucα1-4)GlcNAcβ1-4GlcNAc; SAα2-3Galβ1-3(Fucα1-4)GlcNAcβ1-4GlcNAc; SAα2-3Galβ1-4(Fucα1-3)GlcNAcβ1-4GlcNAc; SAα2-3Galβ1-3(Fucα1-4)GlcNAcβ1-4Gal; SAα2-3Galβ1-4(Fucα1-3)GlcNAcβ1-4Gal; SAα2-3Galβ1-4GlcNAcβ1-3Galβ1-4(Fucα1-3)GlcNAc; SAα2-6Galβ1-4GlcNAcβ1-3Galβ1-4(Fucα1-3)GlcNAc; SAα2-3Galβ1-4(Fucα1-3)GlcNAcβ1-3Galβ1-4Glc; SAα2-6Galβ1-4(Fucα1-3)GlcNAcβ1-3Galβ1-4Glc; SAα2-3Galβ1-4GlcNAcβ1-3Galβ1-4(Fucα1-3)GlcNAcβ1-3Galβ1-4Glc; SAα2-6Galβ1-4GlcNAcβ1-3Galβ1-4(Fucα1-3)GlcNAcβ1-3Galβ1-4Glc; SAα2-3Galβ1-4(Fucα1-3)GlcNAcβ1-3Galβ1-4(Fucα1-3)GlcNAcβ1-3Galβ1-4Glc; SAα2-6Galβ1-4(Fucα1-3)GlcNAcβ1-3Galβ1-4(Fucα1-3)GlcNAcβ1-3Galβ1-4Glc; SAα2-3Galβ1-4(Fucα1-3)GlcNAcβ1-3Galβ1-4Glc; SAα2-6Galβ1-4(Fucα1-3)GlcNAcβ1-3Galβ1-4Glc; SAα2-3Galβ1-4GlcNAcβ1-3Galβ1-4(Fucα1-3)GlcNAcβ1-3Galβ1-4(Fucα1-3)GlcNAcβ1-3Galβ1-4Glc; SAα2-3Galβ1-3(Fucα1-4)GlcNAc; SAα2-6Galβ1-3(Fucα1-4)GlcNAc; SAα2-3Galβ1-3GlcNAcβ1-4Galβ1-4(Fucα1-3)GlcNAc; SAα2-6Galβ1-3GlcNAcβ1-4Galβ1-4(Fucα1-3)GlcNAc; SAα2-3Galβ1-3(Fucα1-4)GlcNAcβ1-3Galβ1-4(Fucα1-3)GlcNAc; SAα2-6Galβ1-3(Fucα1-4)GlcNAcβ1-3Galβ1-4(Fucα1-3)GlcNAc; SAα2-3Galβ1-3(Fucα1-4)GlcNAcβ1-3Galβ1-4Glc; SAα2-6Galβ1-3(Fucα1-4)GlcNAcβ1-3Galβ1-4Glc; SAα2-3Galβ1-3GlcNAcβ1-4Galβ1-4(Fucα1-3)GlcNAcβ1-3Galβ1-4Glc; SAα2-6Galβ1-3GlcNAcβ1-4Galβ1-4(Fucα1-3)GlcNAcβ1-3Galβ1-4Glc; SAβ2-3Galβ1-3(Fucα1-4)GlcNAcβ1-3Galβ1-4(Fucα1-3)GlcNAcβ1-3Galβ1-4Glc; SAα2-6Galβ1-3(Fucα1-4)GlcNAcβ1-3Galβ1-4(Fucα1-3)GlcNAcβ1-3Galβ1-4Glc; SAα2-3Galβ1-3(Fucα1-4)GlcNAcβ1-3Galβ1-4(Fucα1-3)Glc; SAα2-6Galβ1-3(Fucα1-4)GlcNAcβ1-3Galβ1-4(Fucα1-3)Glc; SAα2-3Galβ1-3GlcNAcβ1-4Galβ1-4(Fucα1-3)GlcNAcβ1-3Galβ1-4(Fucα1-3)Glc; SAα2-6Galβ1-3GlcNAcβ1-4Galβ1-4(Fucα1-3)GlcNAcβ1-3Galβ1-4(Fucα1-3)Glc; SAα2-3Galβ1-3(Fucα1-4)GlcNAcβ1-3Galβ1-4(Fucα1-3)GlcNAcβ1-3Galβ1-4(Fucα1-3)Glc; SAα2-6Galβ1-3(Fucα1-4)GlcNAcβ1-3Galβ1-4(Fucα1-3)GlcNAcβ1-3Galβ1-4(Fucα1-3)Glc; SAα2-3Galβ1-4GlcNAcβ1-3Galβ1-3(Fucα1-4)GlcNAc; SAα2-6Galβ1-4GlcNAcβ1-3Galβ1-3(Fucα1-4)GlcNAc; SAα2-3Galβ1-4(Fucα1-3)GlcNAcβ1-3Galβ1-3(Fucα1-4)GlcNAc; SAα2-6Galβ1-4(Fucα1-3)GlcNAcβ1-3Galβ1-3(Fucα1-4)GlcNAc; SAα2-3Galβ1-4GlcNAcβ1-3Galβ1-3(Fucα1-4)GlcNAcβ1-3Galβ1-4Glc; SAα2-6Galβ1-4GlcNAcβ1-3Galβ1-3(Fucα1-4)GlcNAcβ1-3Galβ1-4Glc; SAα2-3Galβ1-4(Fucα1-3)GlcNAcβ1-3Galβ1-3(Fucα1-4)GlcNAcβ1-3Galβ1-4Glc; SAα2-6Galβ1-4(Fucα1-3)GlcNAcβ1-3Galβ1-3(Fucα1-4)GlcNAcβ1-3Galβ1-4Glc; SAα2-3Galβ1-4(Fucα1-3)GlcNAcβ1-3Galβ1-3(Fucα1-4)Glc; SAα2-6Galβ1-4(Fucα1-3)GlcNAcβ1-3Galβ1-3(Fucα1-4)Glc; SAα2-3Galβ1-3GlcNAcβ1-4Galβ1-4(Fucα1-3)Glc; SAα2-3Galβ1-3GlcNAcβ1-3Galβ1-4(Fucα1-3)Glc; SAα2-6Galβ1-3GlcNAcβ1-4Galβ1-4(Fucα1-3)GlcNAcβ1-3Galβ1-4(Fucα1-3)Glc; SAα2-3Galβ1-4(Fucα1-3)GlcNAcβ1-3Galβ1-3(Fucα1-4)GlcNAcβ1-3Galβ1-4(Fucα1-3)Glc; SAα2-6Galβ1-4GlcNAcβ1-3Galβ1-3(Fucα1-4)GlcNAcβ1-3Galβ1-4(Fucα1-3)Glc; SAα2-3Galβ1-4(Fucα1-3)GlcNAcβ1-3Galβ1-3(Fucα1-4)GlcNAcβ1-3Galβ1-4(Fucα1-3)Glc; and SAα2-6Galβ1-4(Fucα1-3)GlcNAcβ1-3Galβ1-3(Fucα1-4)GlcNAcβ1-3Galβ1-4(Fucα1-3)Glc, where SA is sialic acid.

In a second preferment of the third aspect of the invention F and the epitope of the antigen are both a peptide. More preferably, the peptide is an oligopeptide. Most preferably, the oligopeptide is selected from the group listed in the Table of Peptides.

In a third preferment of the third aspect of the invention F is a conjugator. More preferably, F is a conjugator that is biotin. When F is a conjugator that is biotin, the biotin may or may not be conjugated to an avidinylated functional moiety.

Preferably, when F is a glycan, S is selected from the group consisting of:

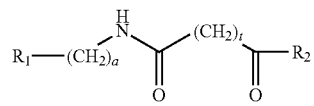

where:

a and b are independently the integer 3, 4 or 5; and $R_1$ and $R_2$ are, respectively, O of the glycan and N of the primary amino of a diacyl or dialkyl-glycerophospholipid or N of the primary amino of a diacyl or dialkyl-glycerophospholipid and O of the glycan, or

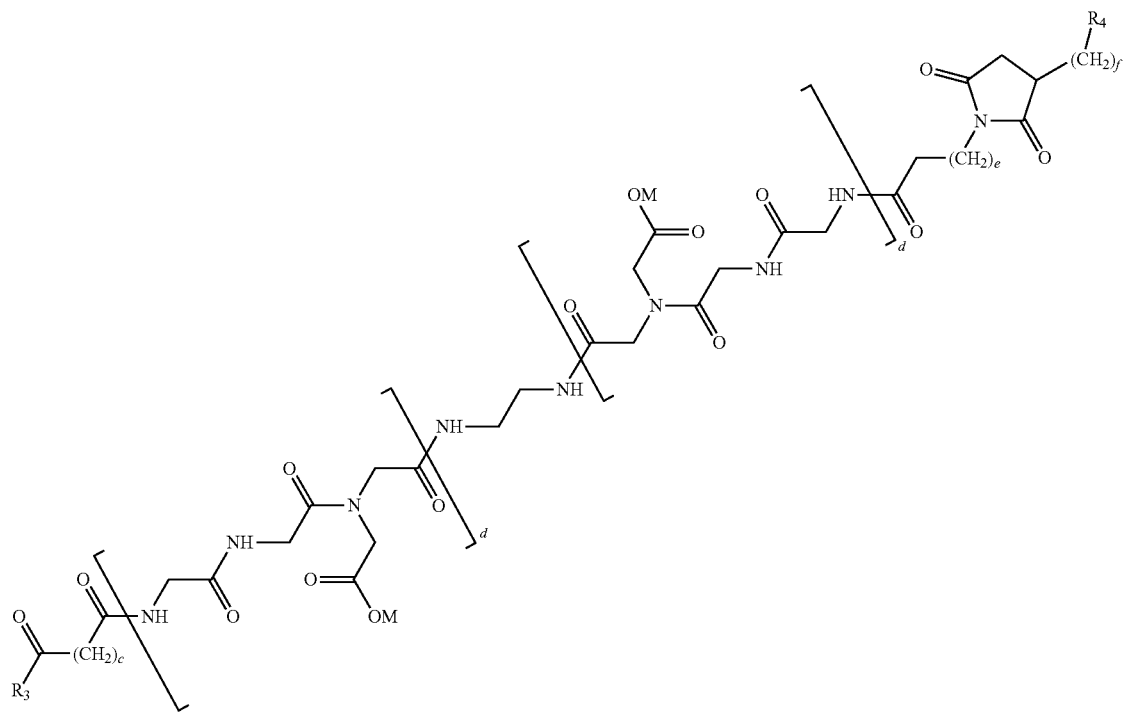
where:
M is $CH_3$ or H;
c is the integer 3, 4 or 5;
d and e are independently the integer 1, 2 or 4;
f is the integer 2, 3 or 4;
$R_3$ is N of the primary amino of a diacyl or dialkyl-glycerophospholipid; and
$R_4$ is O of the glycan.
Preferably, when F is a peptide, S is selected from the group consisting of:
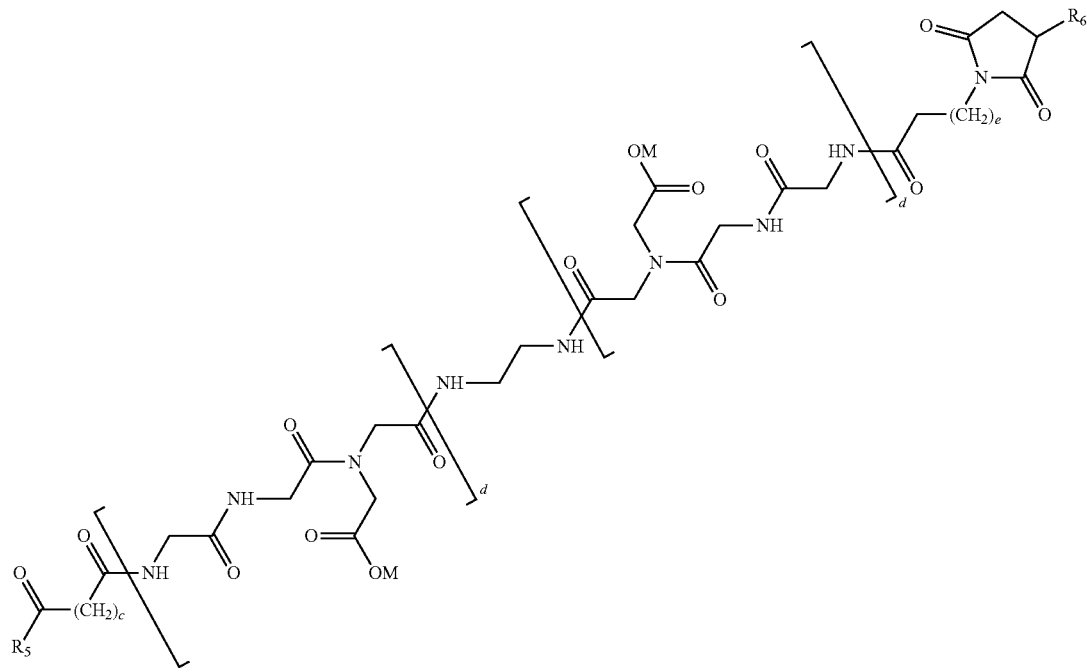

where:
- M is $CH_3$ or H;
- c is the integer 3, 4 or 5;
- d and e are independently the integer 1, 2 or 4;
- $R_5$ is N of the primary amino of a diacyl or dialkyl-glycerophospholipid; and
- $R_6$ is S of the sulfhydryl of an amino acid residue of the peptide,

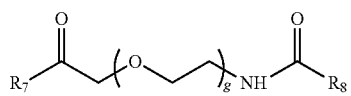

where:
- g is a value in the range 6 to 14;
- $R_7$ and $R_8$ are, respectively, N of the amino terminus of the peptide and N of the primary amino of a diacyl or dialkyl-glycerophospholipid or N of the primary amino of a diacyl or dialkyl-glycerophospholipid and N of the amino terminus of the peptide, $R_9$ is N of the primary amino of a diacyl or dialkyl-glycerophospholipid; and $R_{10}$ is S of the sulfhydryl of an amino acid residue of the peptide, or

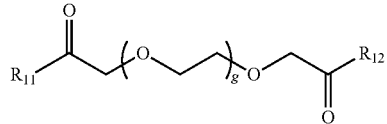

g is a value in the range 6 to 14;

$R_{11}$ and $R_{12}$ are, respectively, N of the amino terminus of the peptide and N of the primary amino of a diacyl or dialkyl-glycerophospholipid or N of the primary amino of a diacyl or dialkyl-glycerophospholipid and N of the amino terminus of the peptide.

Preferably, when F is a conjugator that is biotin, F-S is selected from the group consisting of:

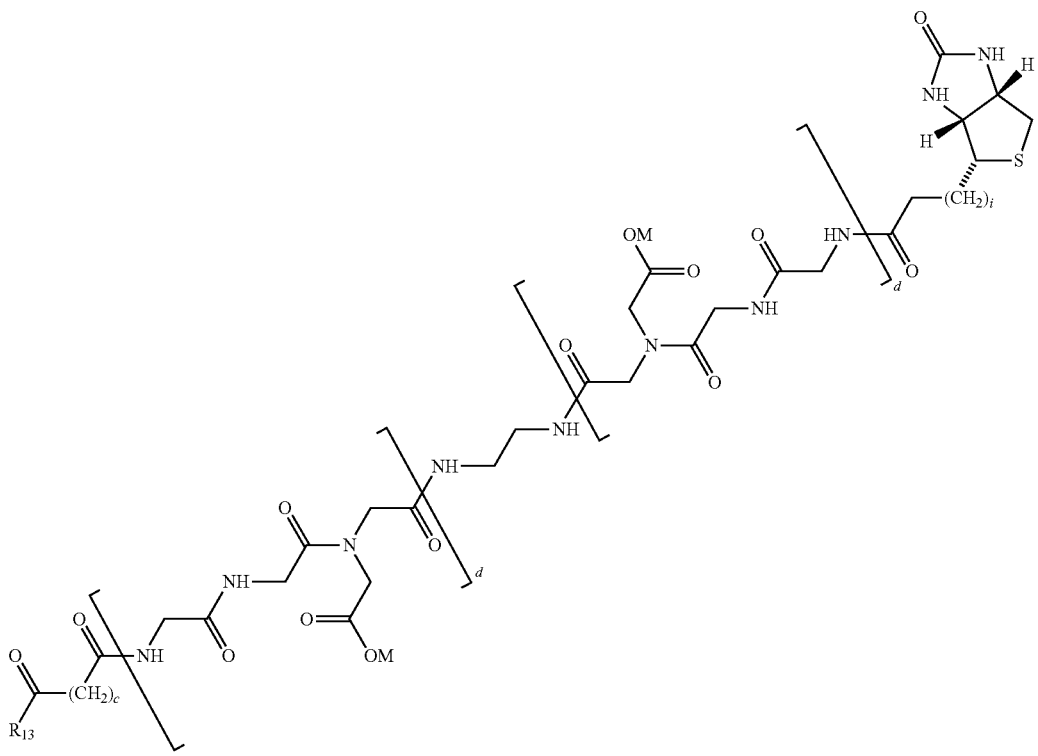

or

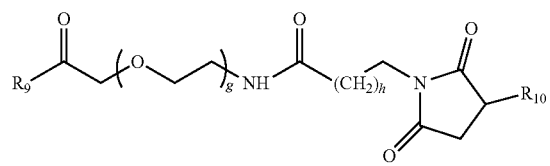

where:
- g is a value in the range 6 to 14;
- h is the integer 1 or 2;

where:
- M is $CH_3$ or H;
- c is the integer 3, 4 or 5;
- d and e are independently the integer 1, 2 or 4; and
- $R_{13}$ is N of the primary amino of a diacyl or dialkyl-glycerophospholipid.

F may or may not include an avidinylated functional moiety.

In a first preferment of the third aspect of the invention F is an epitope of an antigen presented at the surface of the cells and the contacting the surface with a suspension of the cells is in the presence of primary antibody cross-reactive with the epitope.

In a second preferment of the third aspect of the invention F is biotin, the cells are biotinylated cells, and the contacting the surface with a suspension of the cells is preceded by contacting either the surface or the cells with an excess of avidin and washing.

In the description and claims of this specification the following abbreviations, acronyms, terms and phrases have the meaning provided: "belt" means, with reference to inkjet printing, the means of attachment between the printhead and stepper motor; "control circuitry" means, with reference to inkjet printing, that part of the printer that controls the mechanical aspects of operation of the printer; "dispersible in water" means a stable, single phase system is formed when the synthetic construct is contacted with water; "glycan" means a polysaccharide or oligosaccharide and includes the carbohydrate portion of a glycoconjugate, such as a glycoprotein, glycolipid, or a proteoglycan; "immobilised" means covalently bound to a surface and "immobilising" and "immobilisation" have a corresponding meaning; "impact" means, with reference to printing on the surface of a substrate, a method of printing where in image is created by a printer mechanism contacting the surface, e.g. character and dot matrix printers; "ink cartridge" means with reference to inkjet printing, that part of the print head assembly comprising a reservoir for containing ink; "inkjet printer" means a non-impact printer that propels droplets of ink onto the surface of a substrate to create an image consisting of a plurality of dots (typically between 45 and 65 µm in diameter; "localised" means associated with a surface by non-covalent interactions and "localising" and "localisation" have a corresponding meaning; "microarray" means a two-dimensional array of small quantities of biological material; "monolithic" means, with reference to a printhead, the plurality of orifices (nozzles) from which droplets of ink are propelled are formed in a single body of material, e.g. a silicon substrate, by means such as photolithography or chemical etching; "non-impact" means, with reference to printing on the surface of a substrate, a method of printing where an image is created without a printer mechanism contacting the surface, e.g. inkjet and laser printers; "picoliter" means a volume of $10^{-12}$ liter (pL); "piezoelectric" means, with reference to inkjet printing, the method of propelling droplets of ink from the orifices (nozzles) of the printhead by vibration of piezo crystals; "polar functional groups" means any one or more of a carbonyl (—C=O), carboxyl (—COOH) or secondary amino (>NH) group; "printhead" means, with reference to inkjet printing, that part of the print head assembly comprising a plurality of orifices (nozzles) from which droplets of ink are propelled; "printhead stepper motor" means, with reference to inkjet printing, that part of the printer that drives the movement of the printhead across the surface of a substrate; "rollers" means, with reference to inkjet printing, a set of rollers operating to advance the surface of a substrate through the transverse path of the printhead; "substrate feed stepper motor" means, with reference to inkjet printing, that part of the printer that drives the rollers to advance the surface of the substrate through the transverse path of the printhead; "thermal bubble" means, with reference to inkjet printing, the method of propelling droplets of ink from the orifices (nozzles) of the printhead by vaporizing a volume of the ink; and "spacer" means a chemical moiety distinct from the base (e.g. ethanolamine) of a glycerophospholipid comprising at least three polar functional groups.

In the description and claims of this specification the amino acids of peptides are identified in accordance with Tables 1 to 4 of Annex C, Appendix 2 of the PCT Administrative Instructions (as in force from Jan. 1, 2010).

The use of the terms "first", "second", "third", etc. with reference to elements, features or integers of the subject matter defined in the Statement of Invention and Claims, or with reference to alternative embodiments or preferments of the invention is intended to distinguish between alternatives and is not intended to imply an order of preference unless specifically stated.

The invention will now be described with reference to the following Table of Peptides, embodiments or examples, and the figures of the accompanying drawings pages.

| Table of Peptides | SEQ ID NO: |
|---|---|
| Cys(Xaa)$_z$TrpThrProProArgAlaGlnIleThrGlyTyrLeuThrValGlyLeuThrArgArg | 1 |
| Cys(Xaa)$_z$TrpThrProProArgAlaGlnIleThrGlyTyrArgLeuThrValGlyLeuThrArgArg | 2 |
| Cys(Xaa)$_z$ValMetTyrAlaSerSerGly | 3 |
| ValMetTyrAlaSerSerGly(Xaa)$_z$Cys | 4 |
| AspTyrHisArgValMetTyrAlaSerSerGly(Xaa)$_z$Cys | 5 |
| ThrAsnGlyGluThrGlyGlnLeuValHisArgPhe(Xaa)$_z$Cys | 6 |
| ThrAsnGlyGluMetGlyGlnLeuValHisArgPhe(Xaa)$_z$Cys | 7 |
| AspThrTyrProAlaHisThrAlaAsnGluValSerGlu(Xaa)$_z$Cys | 8 |
| ThrTyrProAlaHisThrAlaAsnGluVal(Xaa)$_z$Cys | 9 |
| ProAlaHisThrAlaAsnGluVal(Xaa)$_z$Cys | 10 |
| TyrProAlaHisThrAlaAsnGlu(Xaa)$_z$Cys | 11 |
| ThrTyrProAlaHisThrAlaAsn(Xaa)$_z$Cys | 12 |
| ThrTyrProAlaHisThrAlaAsnGlu(Xaa)$_z$Cys | 13 |
| TyrProAlaHisThrAlaAsnGluVal(Xaa)$_z$Cys | 14 |
| ProAlaHisThrAlaAsnGluValSer(Xaa)$_z$Cys | 15 |
| AspThrTyrProAlaHisThrAlaAsnGlu(Xaa)$_z$Cys | 16 |
| TyrProAlaHisThrAlaAsnGluValSer(Xaa)$_z$Cys | 17 |
| SerGlnThrAsnAspLysHisLysArgAsp(Xaa)$_z$Cys | 18 |
| GlnThrAsnAspLysHisLysArgAspThrTyr(Xaa)$_z$Cys | 19 |
| GlnThrAsnAspLysHisLysArgAspThrTyrSerSerGlnThrAsnAspMetHisLysArgAspThrTyr(Xaa)$_z$Cys | 20 |
| GlnThrAsnAspMetHisLysArgAspThrTyr(Xaa)$_z$Cys | 21 |
| SerSerGlnThrAsnAspLysHisLysArg(Xaa)$_z$Cys | 22 |
| SerSerGlnThrAsnAspLysHisLysArgAspThrTyr(Xaa)$_z$Cys | 23 |
| SerSerGlnThrAsnAspMetHisLysArgAspThrTyr(Xaa)$_z$Cys | 24 |
| SerSerGlnThrAsnAspLysHisLysArgAspThrTyrSerSerGlnThrAsnAspMetHisLysArgAspThrTyr(Xaa)$_z$Cys | 25 |
| GlnThrAsnAspLysHisLysArgAspThr(Xaa)$_z$Cys | 26 |
| SerGlnThrAsnAspLysHisLysArgAspThr(Xaa)$_z$Cys | 27 |
| ThrAsnAspLysHisLysArgAspThrTyrPro(Xaa)$_z$Cys | 28 |
| GluGluThrGlyGluThrGlyGlnLeuVal(Xaa)$_z$Cys | 29 |

-continued

| Table of Peptides | SEQ ID NO: |
|---|---|
| GluGluGluThrGlyGluThrGlyGlnLeu(Xaa)_Cys | 30 |
| GluThrGlyGluThrGlyGlnLeuValHis(Xaa)_Cys | 31 |
| SerProProArgArgAlaArgValThr(Xaa)_Cys | 32 |
| TyrArgTyrArgTyrThrProLysGluLysThrGlyProMetLysGlu(Xaa)_Cys | 33 |
| TrpGlnProProArgAlaArgIle(Xaa)_Cys | 34 |
| ThrIleThrGlyLeuGluProGlyThrGlu(Xaa)_Cys | 35 |

BRIEF DESCRIPTION OF DRAWINGS

Figure 2:
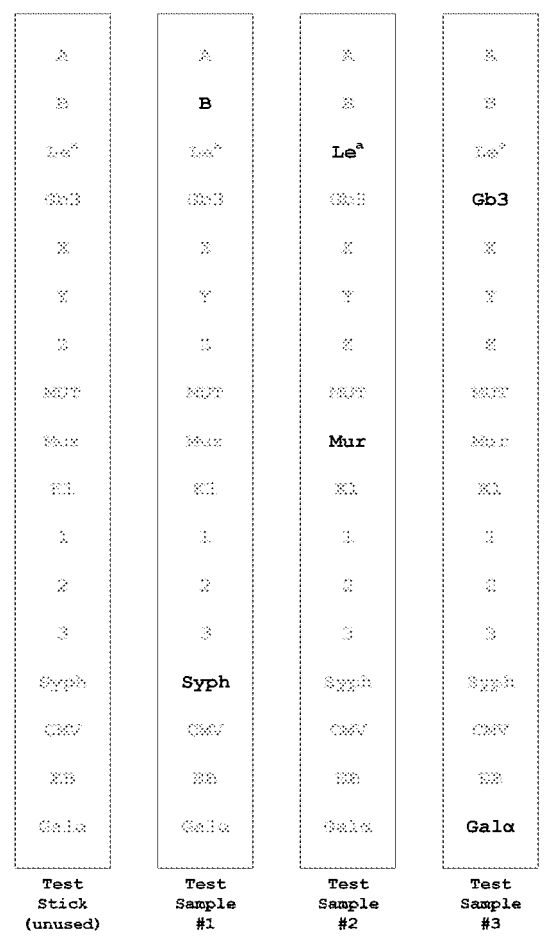

FIG. 2. Diagrammatic illustration of patterning of water dispersible synthetic constructs to provide test strips capable of identifying the presence of a plurality of binding molecules in a test sample.

FIGS. 13A and 13B. Immunostaining with alkaline phosphatase conjugated streptavidin of the surface of substrates (nitrocellulose, silica and paper) printed with a dispersion of FSL-Biotin. The identity of the substrate employed is identified by the words appearing following immunostaining: Silica (Ai and Aii), Sapphire paper (Spicers) (B), Impress Silk paper (Spicers) (C), Sapphire Cast Impress Gloss paper (Spicers) (D), G-Print Matt paper (G), uncoated printer paper (K) and nitrocellulose (L).

DETAILED DESCRIPTION

Figure 1:
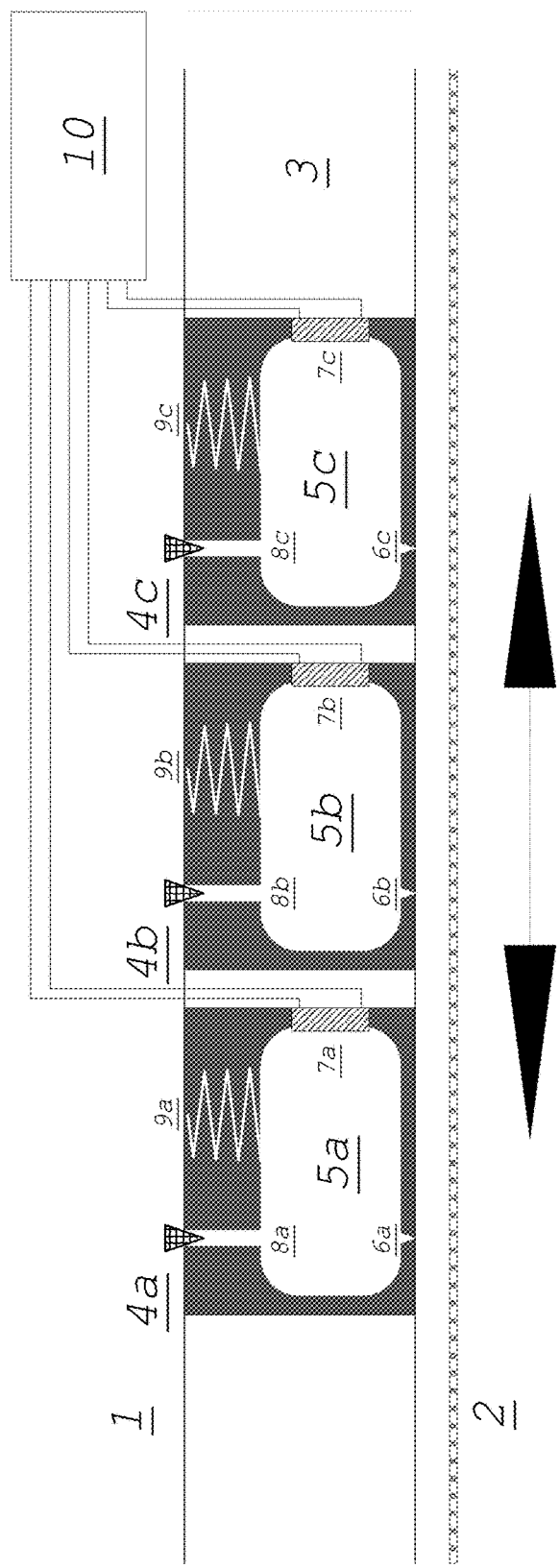
FIG. 1. Schematic representation of a conventional inkjet printer adapted for use in a method of fabricating microarrays in accordance with the method of the invention.
Figure 3:
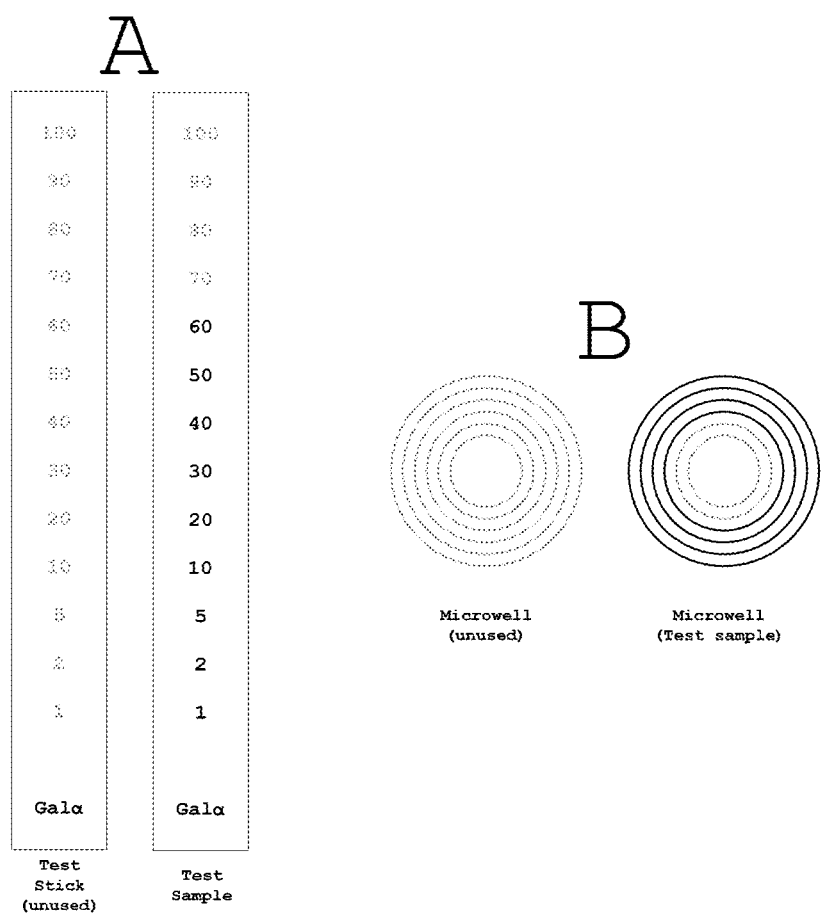
FIG. 3. Diagrammatic illustration of patterning of water dispersible synthetic constructs to provide (A) test strips, and (B) multi-well microplates, capable of use in determining the titre a binding molecule in a test sample.

The advantages provided by the invention arise from the favourable working interrelationship between a combination of features. Firstly, the synthetic constructs of the structure F-S-L are readily dispersible in water ("water soluble" as defined herein). Secondly, the synthetic constructs remain localised to the surface of a substrate despite washing with aqueous solutions. Thirdly, inkjet printer technology has proven to be readily adaptable as a means of applying the dispersions of the synthetic constructs to the surface of the substrate.

Adopting the analogy with conventional inkjet printing the dispersions of synthetic constructs are used as an "ink" to print on the surface of a substrate used as "paper". Indeed it has been discovered that the synthetic constructs are localised to the surface of paper with sufficient strength that the functional moiety is not washed away during blocking and washing steps routinely used in diagnostic assays. The use of existing inkjet printer technology permits the numbers of functional moieties to be localised to the surface of the substrate with greater control and accuracy. The ability to accurately control both the quantity and location of functional moieties localised to the surface of a substrate also permits the printing of "images" that improve the accuracy and reliability of assay results.

The preparation of water dispersible synthetic constructs F-S-L with a range of functional moieties (F) including biotin, glycans and peptides is described in the specifications accompanying international application nos. PCT/NZ2005/000052 (publ. no. WO2005/090368), PCT/NZ2006/000245 (publ. no. WO2007/035116) and PCT/NZ2008/000266 (publ. no. WO 2009/048343).

The selection of a spacer (S) provides a synthetic construct that is readily dispersible in water. It is also apparent that "printed" synthetic constructs are oriented to permit interaction between the functional moiety (F) with a putative binding molecule.

The method of the invention provides the advantage that the requirement for subsequent blocking of unreacted groups on a chemically activated surface (cf. chemical immobilisation) is negated.

An additional advantage is the prospect of eluting binding molecule bound to its target functional moiety from the surface by the use of solvents. The opportunity to then characterise the functional moiety and binding molecule arises.

The use of the chemistry employed in the manufacture of conventional reverse phase media such as $C_8$, $C_{18}$, etc. was initially considered to be most appropriate for the preparation of lipophilic surfaces to which the constructs could be localised. In this context it should be noted that the term "lipophilic" is being used to encompass any chemistry that provides a surface with a strong affinity for the lipid (L) of the synthetic construct. It is to be recognised that some substrates provide a lipophilic surface without the requirement for chemical modification, e.g. nitrocellulose (Fukui et al (2005)) and polystyrene (Huang et al (2006)). The term "lipophilic" as used herein is to be understood as a functional feature. Of particular note in the context of the present invention is that both coated and uncoated printer paper have been demonstrated to provide a suitable "lipophilic" surface.

The monomeric dissociation constant ($K_D$) in a carbohydrate-protein interaction is typically in the millimolar (mM) range. Carbohydrate mediated biological responses often occur through multivalent interactions on the cell surface in order to achieve high affinity and specificity (Chung-Yi et al (2009)). It is anticipated that localising the functional moieties to the surface of a substrate by the interaction of the lipophilic surface and the lipid moiety of the synthetic construct F-S-L permits the functional moieties of a population of deposited synthetic constructs to have a greater opportunity to participate in multivalent interactions with binding molecules, e.g. glycan binding proteins (GBPs).

The adaptation of existing inkjet printing technology to deposit quantities of a dispersion of synthetic construct provides a convenient and cost effective means of fabricating diagnostic test cards and sticks, microarrays and multiwell plates of standard dimensions. Indeed it will be recognised by analogy with conventional colour inkjet printing that the patterning of deposition is also readily achievable. Chambers containing dispersions of populations of synthetic construct are substituted for the colour cartridges of the inkjet printer. Chamber size and design can be readily optimised for the fabrication of microarrays and use of aqueous dispersions. The inclusion of a relatively volatile solvent in the aqueous dispersion is anticipated to facilitate fabrication of the microarrays by promoting evaporation of the vehicle. However, as conventional inject technology permits the delivery of droplets of small size the surface area to volume ratio results in a sufficient rate of evaporation to permit the use of water as a vehicle for the dispersions.

Printheads of designs adaptable for use in the method of the present invention are well described. A description of the adaptation of an inkjet printer for use in the fabrication of microarrays in accordance with the method of the invention will now be described with reference to FIG. 1 of the accompanying drawings.

FIG. 1 is a side cross-sectional view schematically showing the printhead (1) of an inkjet printer and the surface of a substrate (2) in juxtaposition. The printhead (1) is mounted on a carriage (3) that permits reciprocating motion (4) of the printhead (1) relative to the surface of the substrate (2).

The printhead (1) comprises a plurality of modules (4a, 4b, 4c) comprising chambers (5a, 5b, 5c), each containing a dispersion of a population of synthetic construct F-S-L. Each chamber (5a, 5b, 5c) includes an orifice (nozzle) (6a, 6b, 6c) through which a droplet of the dispersion is discharged when a voltage is applied to a piezoelectric assembly (7a, 7b, 7c) in fluid communication with the dispersion.

Each chamber (5a, 5b, 5c) additionally includes a sealable port (8a, 8b, 8c) through which the contents of the chamber may be replenished and a convoluted channel (9a, 9b, 9c) to provide for pressure equalisation subsequent to the discharge of a droplet.

The application of a voltage to each of the piezoelectric assemblies (7a, 7b, 7c) is under the control of a controller (10). In turn the controller and reciprocating motion of the printhead relative to the surface of the substrate are under computer control to permit patterning of the surface of the substrate (2).

The application by the controller (10) of a voltage to the piezoelectric assembly (7a) causes a droplet of predetermined size to be discharged via the orifice (6a) with sufficient momentum to traverse the distance to the juxtaposed surface (2).

On contact with the lipophilic surface it is anticipated the synthetic constructs F-S-L will orient so that the lipid moiety (L) is associated with the surface. This dynamic process is promoted by evaporation of the aqueous vehicle and will be dependent on ambient conditions of temperature and pressure as well as droplet volume as well as the percentage, if any, of co-solvent, e.g. methanol, present in the aqueous vehicle.

It will be apparent from the foregoing description that droplets consisting of different populations of synthetic construct may be deposited in the same discrete area on the surface of the substrate. Microarrays with patterning of this type may be of assistance in identifying binding molecules that form multivalent interactions with a plurality of receptors present in the glycocalyx of cells.

Similarly it will be apparent from the foregoing description that droplets consisting of different populations of synthetic construct may be deposited in the discrete areas spaced apart on the surface of the substrate and at different concentrations. Microarrays with patterning of this type may be of assistance in identifying the avidity and specificity of binding molecules.

As discussed above the non-covalent localisation of functional moieties to a surface presents the prospect of eluting the binding molecule bound to its target functional moiety from the surface. The opportunity to characterise the functional moiety and binding molecule then arises.

In anticipated embodiments the method is used to conveniently and cost effectively produce diagnostic test cards and strips and arrays of the type illustrated diagrammatically in FIG. 2 and FIG. 3.

The diagnostic test cards and strips and arrays may be produced in large numbers with a high degree of reproducibility making them eminently suitable for use in inter-laboratory standardisation.

Reliability and ease of use also suggests the use of the diagnostic test cards and strips and arrays in over-the-counter home test kits.

The patterning of the different populations of synthetic construct may be readily adjusted to correspond to the format of the automated reading device where one is to be used.

In use a test sample is contacted with the diagnostic test strip or array for a predetermined time to allow binding of binding molecules present in the test sample to bind to the functional moiety, e.g. glycotope, of the deposited synthetic construct.

The surface of the diagnostic test strip or array is then washed with an aqueous buffer, such washing facilitated by the lipophilicity of the surface of the test strip or array.

The presence of bound binding molecule may then be detected by use of detection systems such as anti-IgG enzyme conjugates that give rise to a chromogenic response in the presence of the appropriate reagents.

It will be recognised that the ability to deposit populations of synthetic constructs in discrete areas conveniently provides a negative control for the assay to be performed.

By way of illustration, if the assay to be performed is a detection of a particular binding molecule in a sample fluid by chromogenic means the non-deposited area in contact with the sample fluid provides the negative control.

Confirmation of the presence of the binding molecule in the sample fluid is provided by the contrast in chromogenic response between the deposited and non-deposited (negative control) area.

Similarly, it will be recognised that a positive control may be incorporated by depositing in a discrete area a population of synthetic construct comprising a functional moiety (F) known to be present at detectable levels in all sample fluids to be tested.

Assurance that the assay has been performed correctly is provided by the contrast in chromogenic response between the deposited (positive control) and non-deposited area.

The discrete area in which the synthetic construct providing for this positive control is deposited may be delineated so as to provide a confirmatory indica to the user, such as a tick symbol or smiley face, or readable phrase.

It will also be recognised that these methods may be readily adapted to enable the localization of cells to discrete areas on the surface of a substrate. With the advent of inkjet technology that permits printing in three dimensions, the surface need not be a planar surface. In broad outline, quantities of a dispersion on synthetic construct are deposited on a surface. In this context the surface may be the surface of a confluent layer of cells. The printed surface is then contacted with an aqueous suspension of cells. The functional moiety of the synthetic construct is selected to provide for the direct or indirect interaction with the cells. A direct interaction occurs where the cells are expressing binding molecules with affinity for the functional moiety of the synthetic construct. An indirect interaction occurs where antibodies or avidin mediate the interaction. In the former indirect interaction the functional moiety of the synthetic construct is an epitope of an antigen expressed at the surface of the cells. In the latter indirect interaction, the functional moiety of the synthetic construct is biotin and the cells have been biotinylated, e.g. by separately contacting the suspension of cells with the same synthetic construct.

EXAMPLES

Enzyme Linked Immunosorbent Assay

Dispersions of the aminopropyl derivatives of blood group A trisaccharide ($A_{tri}$-$S_1$) and blood group B trisaccharide ($B_{tri}$-$S_1$) were prepared at a concentration of 0.6 mM in phosphate buffered saline (pH 7.2) (PBS). A solution of the construct $A_{tri}$-sp-Ad-DOPE (FSL-A) was also prepared at a concentration of 0.6 mM in PBS.

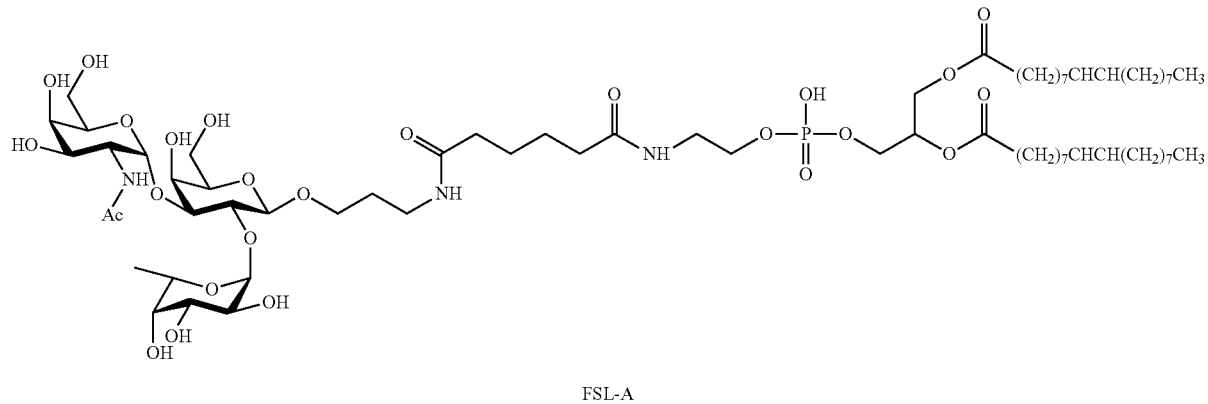

FSL-A

The solutions were applied using a fine tipped artist's paintbrush onto the surface of each of three substrates:
1. Aluminium-backed silica gel thin layer chromatography plates (Alugram Nano-SIL G silica TLC plate, 0.2 nm Nano silica gel 60, Macherey-Nagel);
2. Aluminium-backed $C_{18}$ derivatised silica gel plates; and
3. Nitrocellulose membranes.

One of the samples of aluminium-backed silica gel thin layer chromatography plates to which the solution had been applied was sprayed with a solution of anisaldehyde. The sprayed plate was heated to 200° C. to visualise staining.

The remaining samples of aluminium-backed silica gel thin layer chromatography plates and aluminium-backed $C_{18}$ derivatised silica gel thin layer chromatography plates to which the solution had been applied were immersed in a solution of PLEXIGUM™ P28 (0.5% isobutyl methacrylate polymer in n-hexane and diethyl ether) for 1 minute and then air dried.

The surface of all samples to which the solutions had been applied were then immersed in a solution of 2% (w/v) bovine serum albumin (BSA) in PBS prior to being flooded with a dilution of anti-A immunoglobulin (EPICLONE™ monoclonal, CSL Limited).

The flooded surfaces of the substrates were then washed with PBS prior to being flooded with a 1:400 dilution of alkaline phosphatase conjugated sheep anti-mouse immunoglobulin (Chemicon) for 30 minutes. The flooded surfaces of the substrates were then washed with PBS followed by a washing of substrate buffer (100 mM Tris, 100 mM NaCl, 50 mM $MgCl_2$, pH 9.5).

Figure 4:
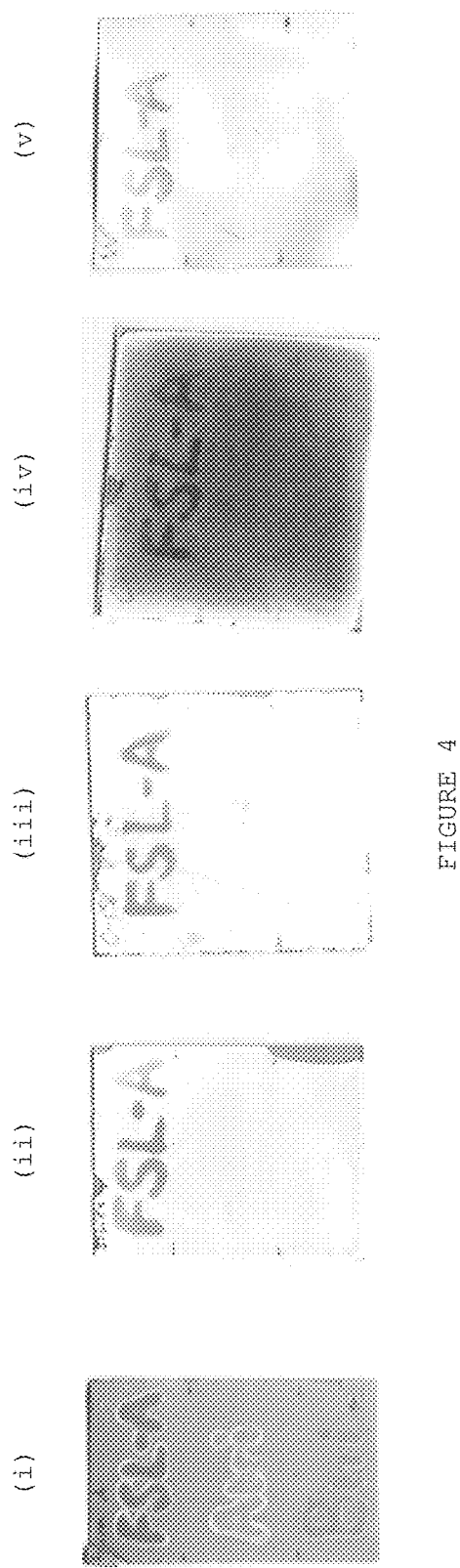
FIG. 4. Appearance of samples of substrate to which solutions of the aminopropyl derivatives of blood group A ($A_{tri}$) and blood group B ($B_{tri}$) trisaccharides and the construct $A_{tri}$-sp-Ad-DOPE (I) (FSL-A) had been applied following visualisation by: i) anisaldehyde (aluminium-backed silica gel plate); ii) immunostaining (aluminium-backed silica gel plate with plasticizer); iii) immunostaining (aluminium backed $C_{18}$ derivatised silica gel plate with plasticizer); iv) immunostaining (aluminium backed $C_{18}$ derivatised silica gel without plasticizer); and v) immunostaining (nitrocellulose).

The substrate buffer washed samples were then flooded with a 1:55 dilution of chromogenic substrate (18.75 mg/mL nitro blue tetrazolium chloride and 9.4 mg/mL 5-bromo-4-chloro-3-indolyl phosphate, toluidine salt) (NBTC-BCIP) for 15 minutes. The appearance of the samples following incubation with substrate is provided in FIG. 4.

Fabrication of Multiwell Plates

Thirty two holes of 7 mm diameter were cut in a 85×63×3 mm planar piece of acrylic in a 4×8 matrix so as to correspond with the positions of half of the wells of a standard multiwell microplate. The upper surface of the planar piece of acrylic was also engraved with letters along the long edge and numbers along the short edge so as to allow each hole in the matrix to be uniquely identified via a two character alphanumeric code. Employing the same template used to direct laser cutting of the planar piece of acrylic, a solution of the construct $A_{tri}$-$S_1$-Ad-DOPE (FSL-A) at a concentration of 1 mg/mL in water was printed onto the surface of an aluminium-backed silica gel plate.

The solution was loaded into the ink cartridge of an EPSON STYLUS™ Colour 460 piezoelectric inkjet printer. A concentration of 0.1% (w/v) bromophenol blue was included to assist in visualising the printed area. The numerals "2" to "9" were printed using the same solution applied at increasing densities (quantity per unit area) corresponding to the grey scale settings of the printer. The alphanumeric character "2" was printed at a grey scale setting of 30% through to the alphanumeric character "9" printed at a grey scale setting of 100%. The printed plate was washed by placing in a beaker of deionised water for a period of 20 minutes and then air dried. The air dried printed plate was then immersed in PLEXIGUM™ P28 for a period of 1 minute before being air dried for a second time. The laser cut planar piece of acrylic was then adhered to the surface of the aluminium-backed painted silica gel plate using multipurpose adhesive. A fabricated 4×8 well microplate was thereby prepared.

Detection of Binding Molecule

Figure 5:
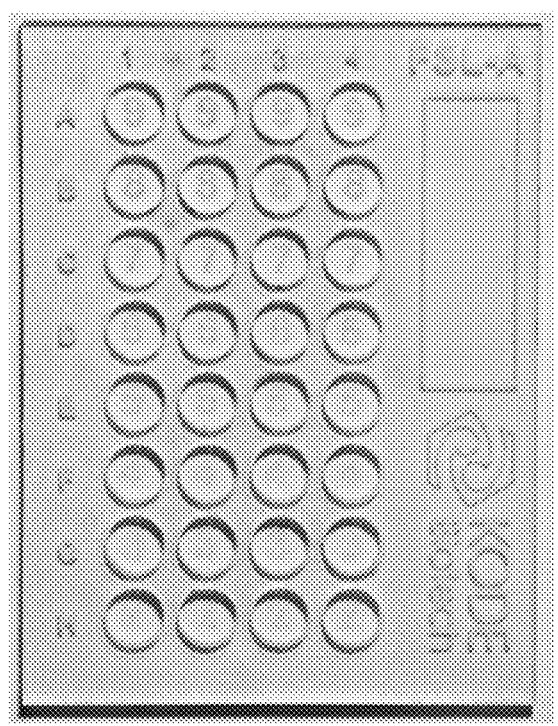
FIG. 5. A multiwell plate fabricated according to the method described showing visualisation of anti-A immunoglobulin binding to $A_{tri}$-sp-Ad-DOPE (I) (FSL-A) applied at increasing densities (quantity per unit area) employing the standard ink cartridge and grey scale setting (30% "2" to 100% "9") of an EPSON Stylus™ Colour 460 printer.

A 100 μL volume of a 2% (w/v) solution of BSA in PBS was dispensed into each well of the fabricated microplate. The plates were incubated for 30 minutes before aspirating the solution of BSA from each well and rinsing. A 100 μL volume of a 1:4 dilution of mouse anti-A immunoglobulin was then dispensed into each well and the plate incubated for 30 minutes before rinsing each well with PBS. A 100 μL volume of a 1:400 dilution of anti-mouse immunoglobulin was then dispensed into each well and the plate incubated for 30 minutes before washing each well with substrate buffer. A 100 μL volume of a 1:55 dilution of chromogenic substrate was then dispensed into each well and the plates incubated for 50 minutes. Each well was finally washed with deionised water and the plate air dried. The air dried plate is presented in FIG. 5.

The method of fabricating described provides for the convenient manufacture of multiwell plates for simultaneous qualitative and quantitative assessment of binding molecules.

Template Design

Different designs of templates for use in the microarray formats can conveniently made in accordance with user requirements employing standard word processing or drawing software packages as illustrated in FIGS. 2, 3 and 5 to 9 of the drawings pages.

Quantitative Antibody Testing

Figure 6:
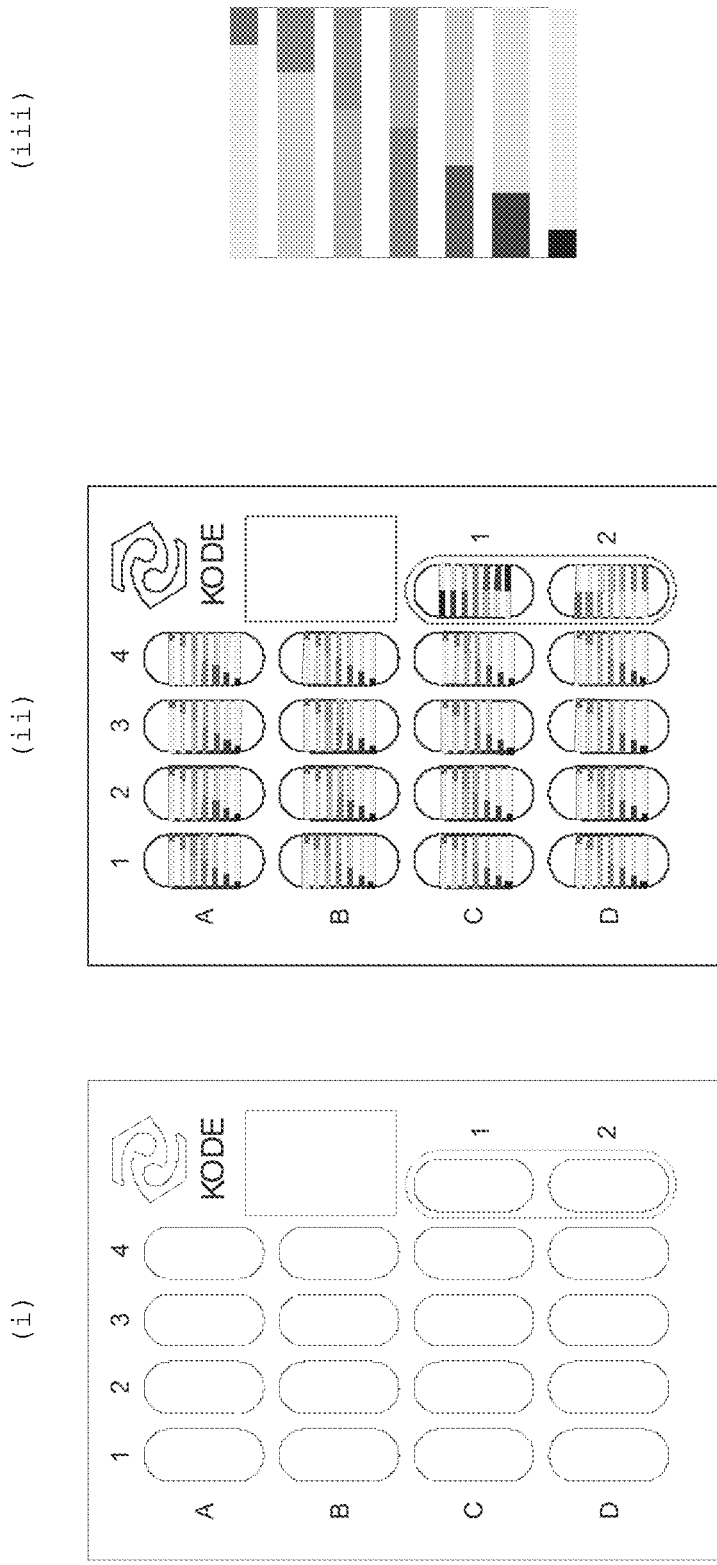
FIG. 6. Template design for use in the fabrication of a multiwell plate for use in quantifying antibody titres.
Figure 7B:
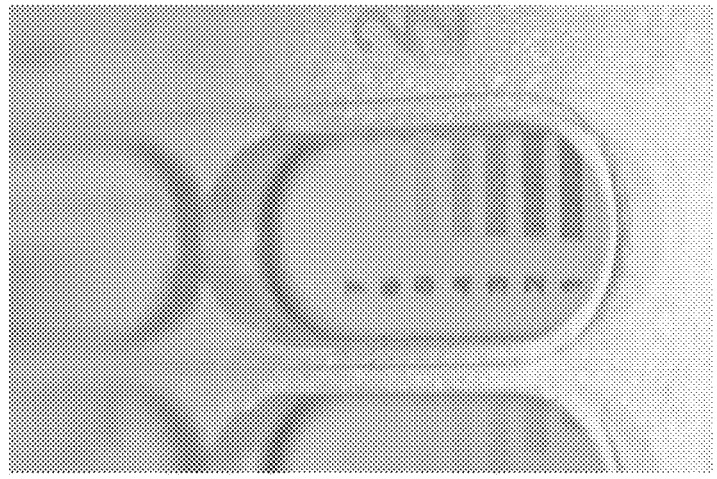
FIG. 7B. An enlargement of one of the wells of the fabricated multiwell plate of FIG. 7A.
Figure 7A:
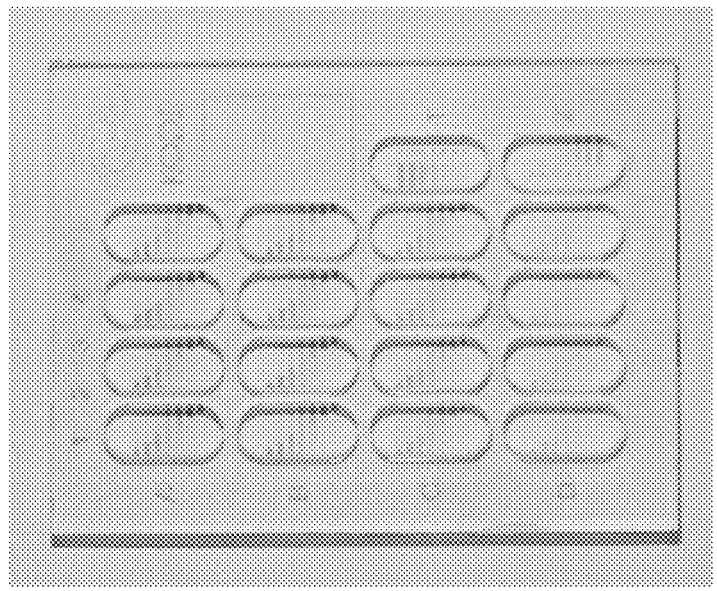
FIG. 7A. A fabricated multiwell plate employing the template of FIG. 6.

By way of illustration of a template design FIG. 6 provides the design of a template for use in quantifying antibody titres. The template is dimensioned to correspond to the dimensions of a standard multiwell microplate. The fabricated multiwell plate may therefore be handled by existing dispensers, washers and camera-based readers of multiwell microplates.

A well of the template corresponds to two wells of a standard multiwell microplate. The two wells on the right of the template may be employed as control wells. The alphanumeric characters and other symbols shown in the template are engraved in the acrylic and the wells are cut out using a laser. The piece of planar acrylic produced is then adhered to a printed silica gel plate.

Solutions of constructs F-S-L are printed employing the same template in which the bars of increasing colour density correspond to increasing densities (quantity per unit area) of construct applied. It will be recognised that the standard gray scale settings of the printer may be employed to provide these increasing densities.

In the template the printing of two constructs is presented. The constructs F-S-L each comprise a different ligand (F) for one or more binding proteins. The binding specificity of one or more binding proteins in the sample may therefore be conveniently assessed.

In the template the two constructs are printed as bars of decreasing density and increasing length.

By the use of the template (and others of comparable design) quantitative assessments of binding may be made in a single well of a multiwell microplate. An internal control (background signal) is provided by the unprinted region outside the discrete area on the surface of the substrate to which the constructs have been applied.

The design of the template also permits monitoring of assays and a convenient means to identify the optimum time to terminate incubations. The controls wells (circled in FIG. 6) have only one of the two construct per well, but printed to provide ladders of increasing density going in both directions. When the middle band appears and a whole line across the well is visible the optimum time to terminate the incubation is indicated.

A fabricated microwell plate employing the design of template illustrated in FIG. 6 and used to determine the titre of antibody according to the method described above is illustrated in FIGS. 7A and 7B.

Well Identification

Figure 8B:
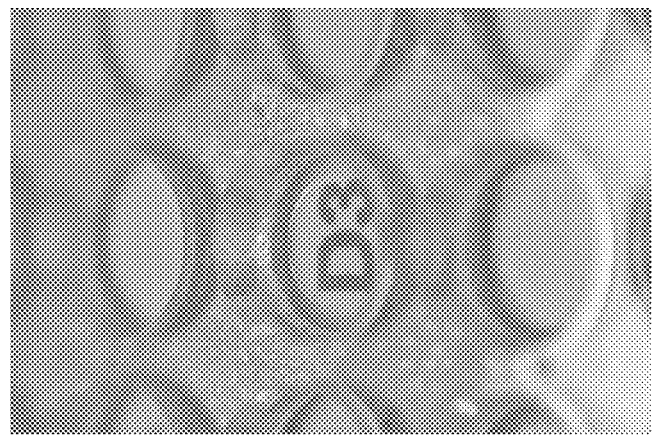
FIG. 8B. An enlargement of one of the wells of the fabricated multiwell plate of FIG. 8A.
Figure 8A:
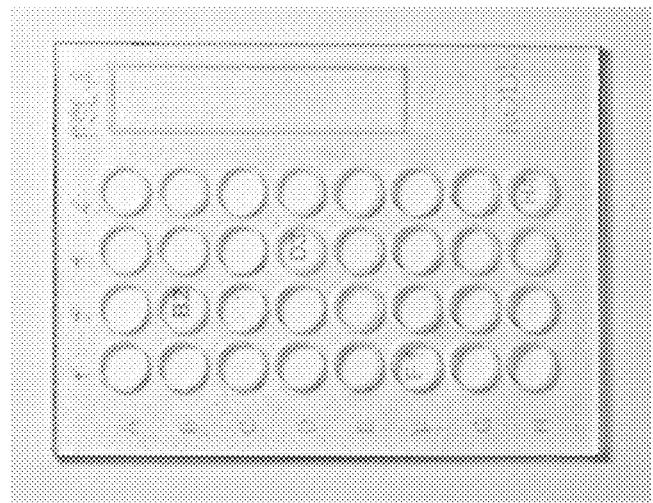
FIG. 8A. A fabricated multiwell plate employing a template to identify the location of each well.

By way of further illustration in circumstances where unequivocal identification of a well in which a positive reaction has occurred is required, a template of the design incorporated into the fabricated multiwell plate illustrated in FIGS. 8A and 8B may be employed.

The alphanumeric combination of characters that appear in wells in which a positive reaction has occurred, unequivocally identify the well without reliance on the user correctly determining the coordinates of the well location. The likelihood of user error in manual operations is thereby greatly reduced.

Detection of Binding Molecule in a Biological Sample

Figure 9:
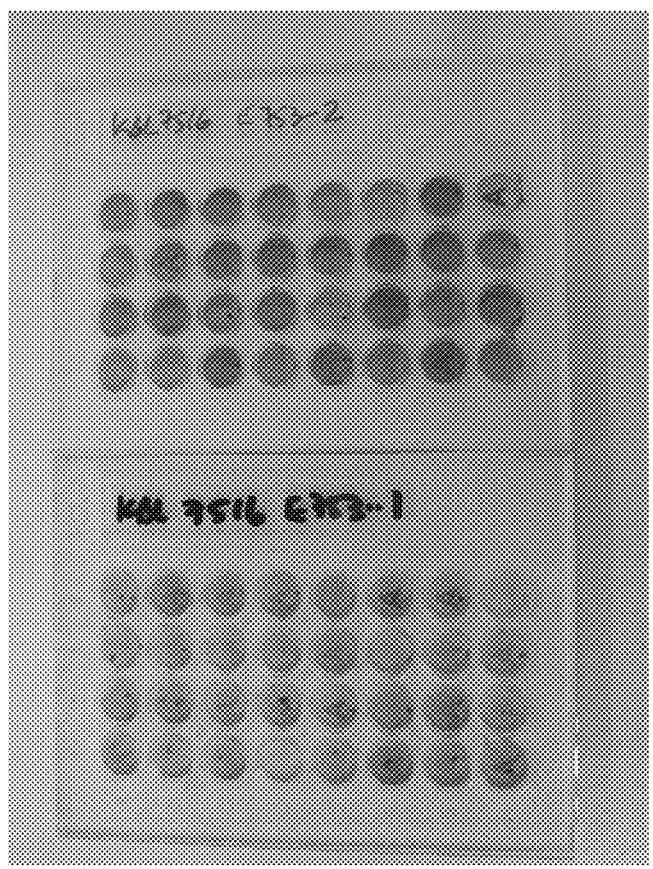
FIG. 9. The fabricated multiwell plates used in the detection of binding molecules in biological samples.
Figure 10:
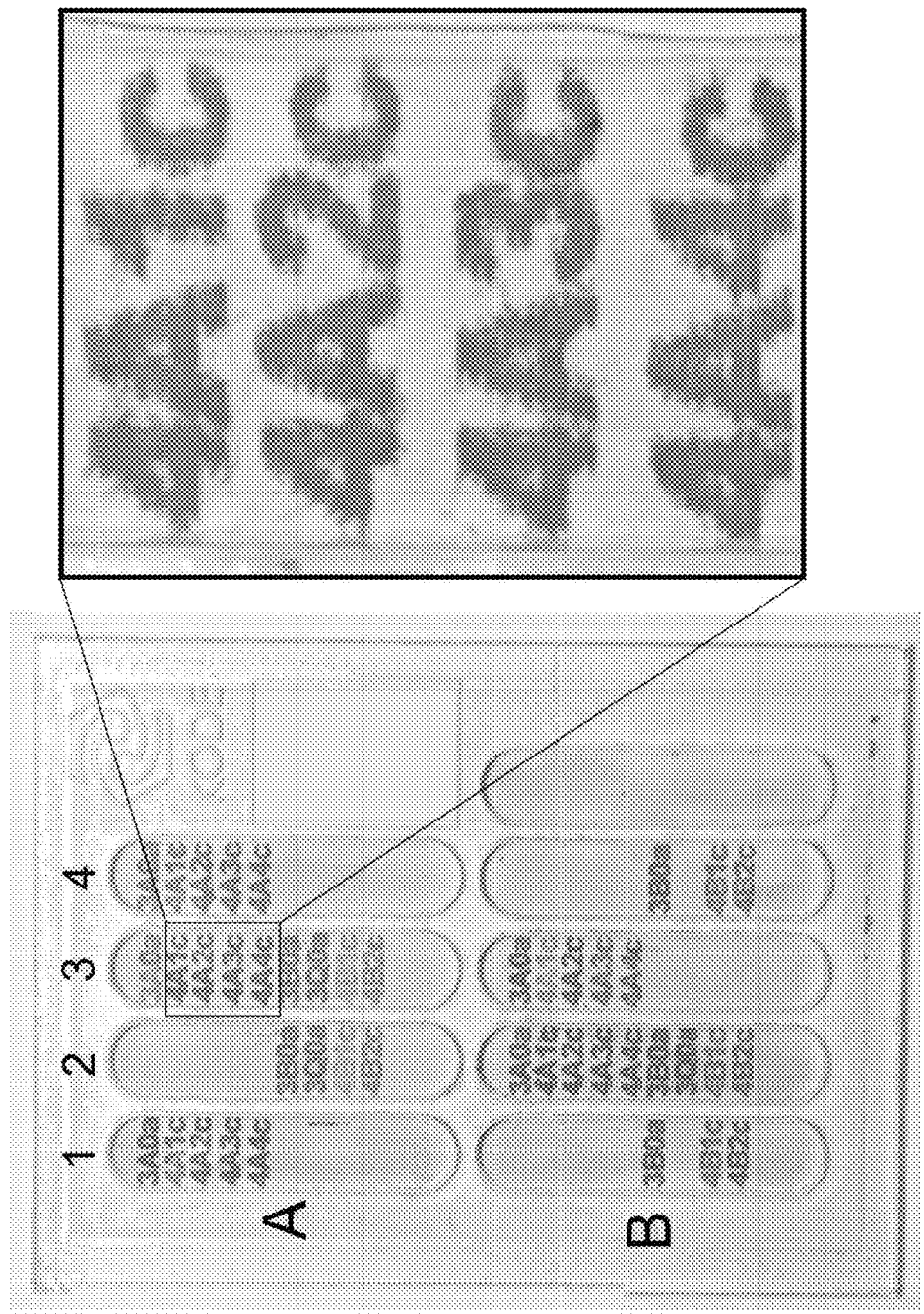
FIG. 10. A microplate prepared with synthetic constructs (where the functional moiety was an epitope of the blood group A or B antigen) printed on paper (MG paper-cellulose esters) to determine specificity of monoclonal reagents. Alphanumeric characters appear when developed in the enzyme linked immunosorbent assay wherever the monoclonal reagent has bound. The area outside of the printed area serves as the "internal" negative control and/or blank. Antibodies in co-ordinates A1, A4, B3 have anti-A specificity, those in A2, B1 and B4 have anti-B specificity while those in A3 and B2 anti-A+B specificity.

To confirm the utility of the fabricated microwell plate in the detection of binding molecules in biological samples the production of anti-A antibody in the serum of mice was elicited by immunisation with A substance saliva. Individual mice were immunised 2, 3 or 4 times with A substance saliva over a three week period. Naïve mice having had no immunisation were used as a control. Elicitation of anti-A antibody in the sera of immunised mice was confirmed by transfusion of modified red blood cells ("kodecytes") according to the methods described in international application no. PCT/NZ2009/000209 [publ. no. WO 2010/039049]. A 32 well microtiter plate was fabricated according to the method described above using a design of template in which the alphanumeric symbol "A" was printed in a location corresponding to the base of each well. Each well was filled with 2% BSA in PBS and incubated at room temperature for at least one hour. Samples of sera collected from immunised mice were diluted 4-fold in 2% BSA in PBS. The 2% BSA in PBS was removed from the wells following incubation and the diluted samples of sera introduced into individual wells using a pipette. The plates were then incubated at room temperature for at least 90 minutes. Following incubation the samples were removed from each well and the plate washed several times with PBS. Excess PBS was removed by blotting of the surface of the plate and each well then filled with a 400-fold dilution of mouse anti-Ig antibody conjugated with alkaline phosphatase. The plates were then incubated for an hour before removing the antibody conjugate solution and washing several times with PBS. The plate was then washed several times with substrate buffer before filling each well of the plate with the chromogenic substrate NBTC-BCIP. The plates were then incubated for 15 to 20 minutes until the printed alphanumeric character appeared. The substrate was then removed and the plate washed under a gentle stream of deionised water and dried. The wells to which anti-A antibody containing samples were introduced were clearly identifiable as illustrated in FIG. 9. It will be recognised that alternative template designs may be developed for the assessment of binding to multiple constructs and the required multiwell microplates conveniently fabricated according to the method described.

Printing on Paper

Figure 11:
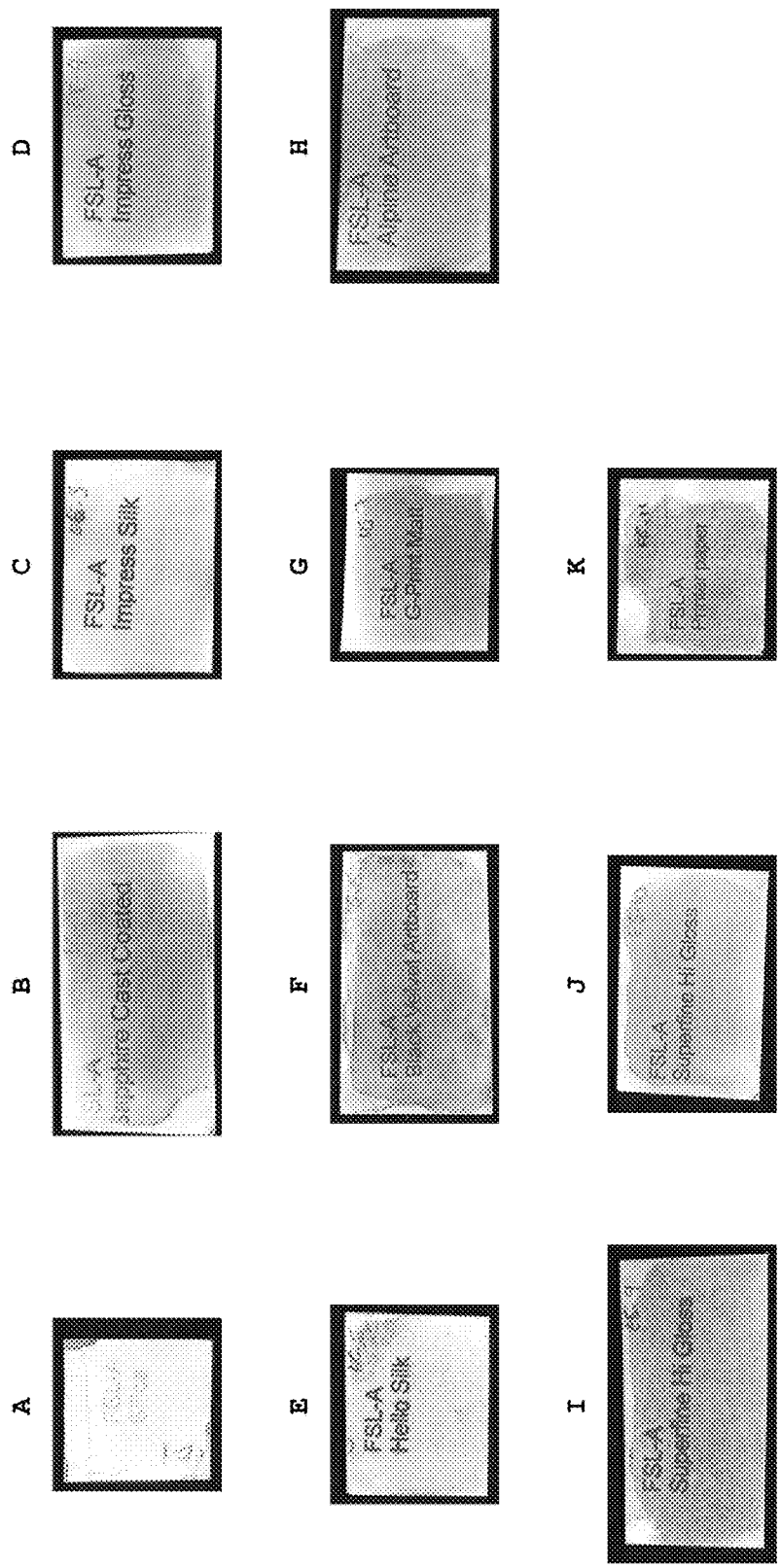
FIG. 11. Immunostaining with monoclonal antibody of the surface of substrates (silica gel and paper) printed with a dispersion of FSL-A. The identity of the substrate employed is identified by the words appearing following immunostaining: silica gel (A), Sapphire Cast Coated (Spicers)(B), Impress Silk (Spicers) (C), Impress Gloss (Spicers)(D), Hello Silk (Spicers)(E), Black Velvet Artboard (F), G-Print Matt (G), Alpine Artboard (H), Superfine Hi Gloss (Spicers)(I and J) and uncoated paper (K).

The ability of standard printing papers to serve as the substrate for use in the method of the invention was evaluated. Solutions of the construct $A_{tri}$-sp-Ad-DOPE (FSL-A) and a solution of the aminopropyl derivative of the A trisaccharide ($A_{tri}$-sp-NH$_2$) were printed on to various types of commercially available printing papers as previously described. An ink jet printer (EPSON STYLUS™ T21) with refillable cartridges modified to hold a smaller volume was employed. The construct $A_{tri}$-sp-Ad-DOPE (FSL-A) and the aminopropyl derivative of the A trisaccharide ($A_{tri}$-sp-NH$_2$) were prepared as solutions at a concentration of 6 mM. Each one of the solutions was used to fill separate modified cartridges permitting both solutions to be printed at the same time on the same sample of paper. To facilitate identification and as an illustration of one of the advantages of the invention the identification of the solution and trade name of the paper employed as the sample were printed. Following printing of the two solutions each sample of paper was blocked with a 2% (w/v) solution of BSA and immunostained with monoclonal anti-A and then anti-mouse IgG conjugated to alkaline phosphatase and the chromogenic substrate NBT-BCIP. The immunostained samples of printed paper are presented in FIG. 11. It will be observed that there was no immunostaining of the sample of printed paper in the region where the aminopropyl derivative of the A trisaccharide ($A_{tri}$-sp-NH$_2$) was printed. It is assumed that the aminopropyl derivative of the A trisaccharide ($A_{tri}$-sp-NH$_2$) was washed away during the blocking step and immunostaining procedure. Although the majority of the papers employed in the study were coated papers it was also demonstrated that normal uncoated paper could also serve as a suitable substrate.

Biological Sample

Figure 12:
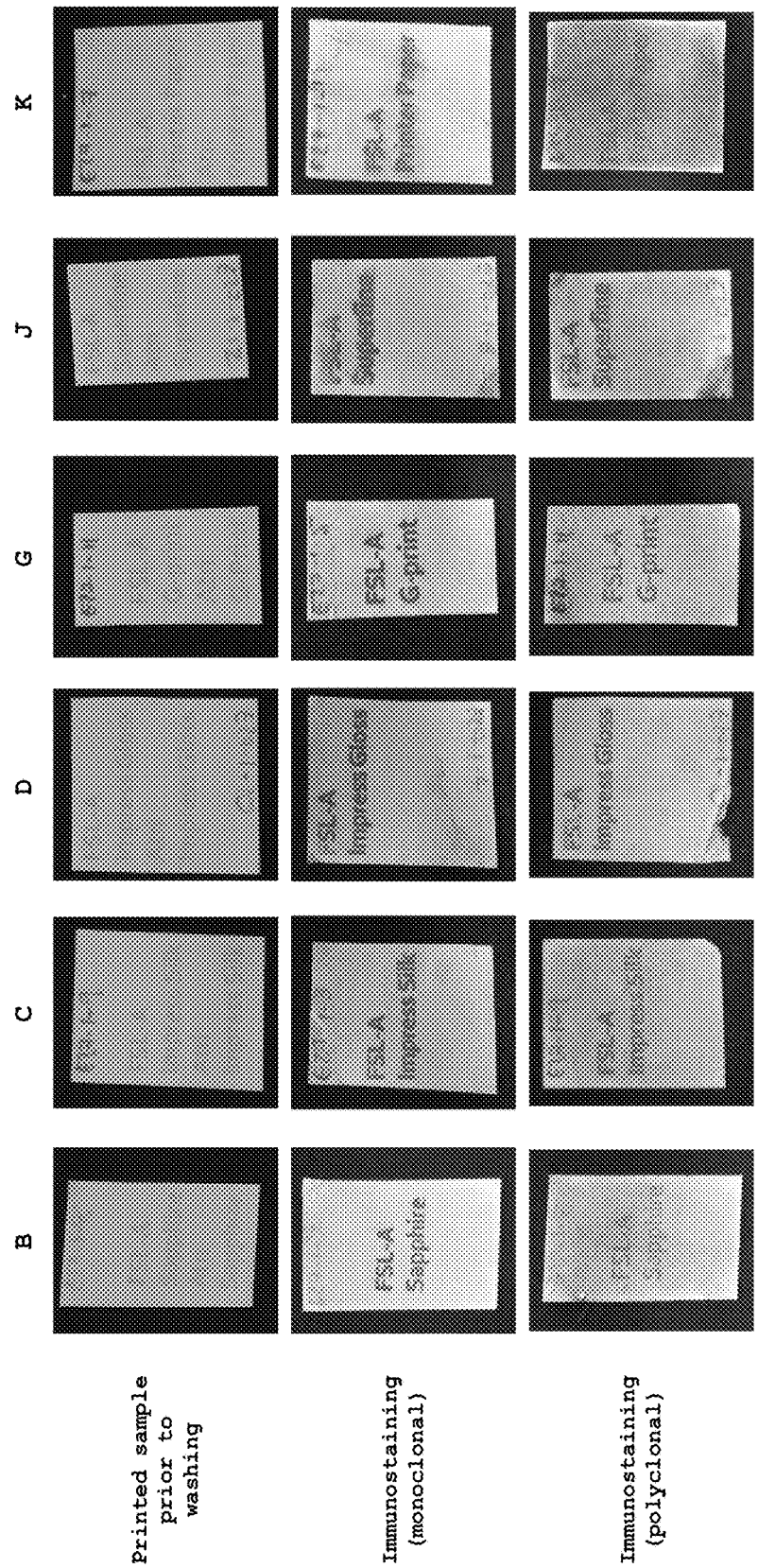
FIG. 12. Immunostaining with monoclonal and polyclonal (serum) antibody of the surface of substrates (paper) printed with a dispersion of FSL-A. The identity of the substrate employed is identified by the words appearing following immunostaining: Sapphire Cast Coated (Spicers) (B), Impress Silk (Spicers) (C), Impress Gloss (Spicers) (D), G-Print Matt (G), Superfine Hi Gloss (Spicers)(J) and uncoated paper (K).

Samples of printed papers were prepared as described under the preceding heading. On this occasion, polyclonal human blood group O serum and mouse anti-human Ig were employed in the immunostaining procedure. A concentration of 0.05% w/v bromophenol blue was included in the solutions of the construct $A_{tri}$-sp-Ad-DOPE (FSL-A) to permit visualisation of the printed solutions. The dye was removed following the initial step of printing by placing the samples of printed paper in a beaker of deionised water for 15 minutes followed by air drying. The dried printed samples of paper were then blocked with a solution of BSA for 30 minutes as previously described. The surface of each sample of printed paper was then flooded with a 1 in 4 dilution of either anti-A monoclonal antibody or the O serum for 60 minutes at room temperature. The flooded surface of the printed sample of paper was then washed repeatedly by flooding the surface of each sample of printed paper with PBS for 20 seconds and rinsing with PBS. A comparison of the appearance of the printed samples of paper at each step of the procedure is presented in FIG. 12. It will be observed that no immunostaining in the region where the aminopropyl derivative of the A trisaccharide ($A_{tri}$-sp-NH$_2$) was printed occurs. The construct $A_{tri}$-sp-Ad-DOPE (I) (FSL-A) is detected following immunostaining with either monoclonal or polyclonal (serum) antibodies. Certain of the coated papers were observed to provide great contrast in the immunostaining procedure when polyclonal (serum) antibodies were employed.

Printing of FSL-Biotin

A dispersion of the construct FSL-Biotin at a concentration of 1 mg/ml (6 mM) in PBS and containing 0.05% (w/v) bromophenol blue was prepared. A volume of the solution was injected into the modified refillable cartridge of a piezoelectric printer (EPSON™ Stylus T21). The dispersion of the construct FSL-Biotin was printed onto samples of coated papers and uncoated paper. The dispersion of the construct FSL-Biotin was also printed onto aluminium-backed silica TLC plates (0.2 mm Nano silica gel 60, Macherey-Nagel) and nitrocellulose membranes (0.02 µL pore size, Invitrogen).

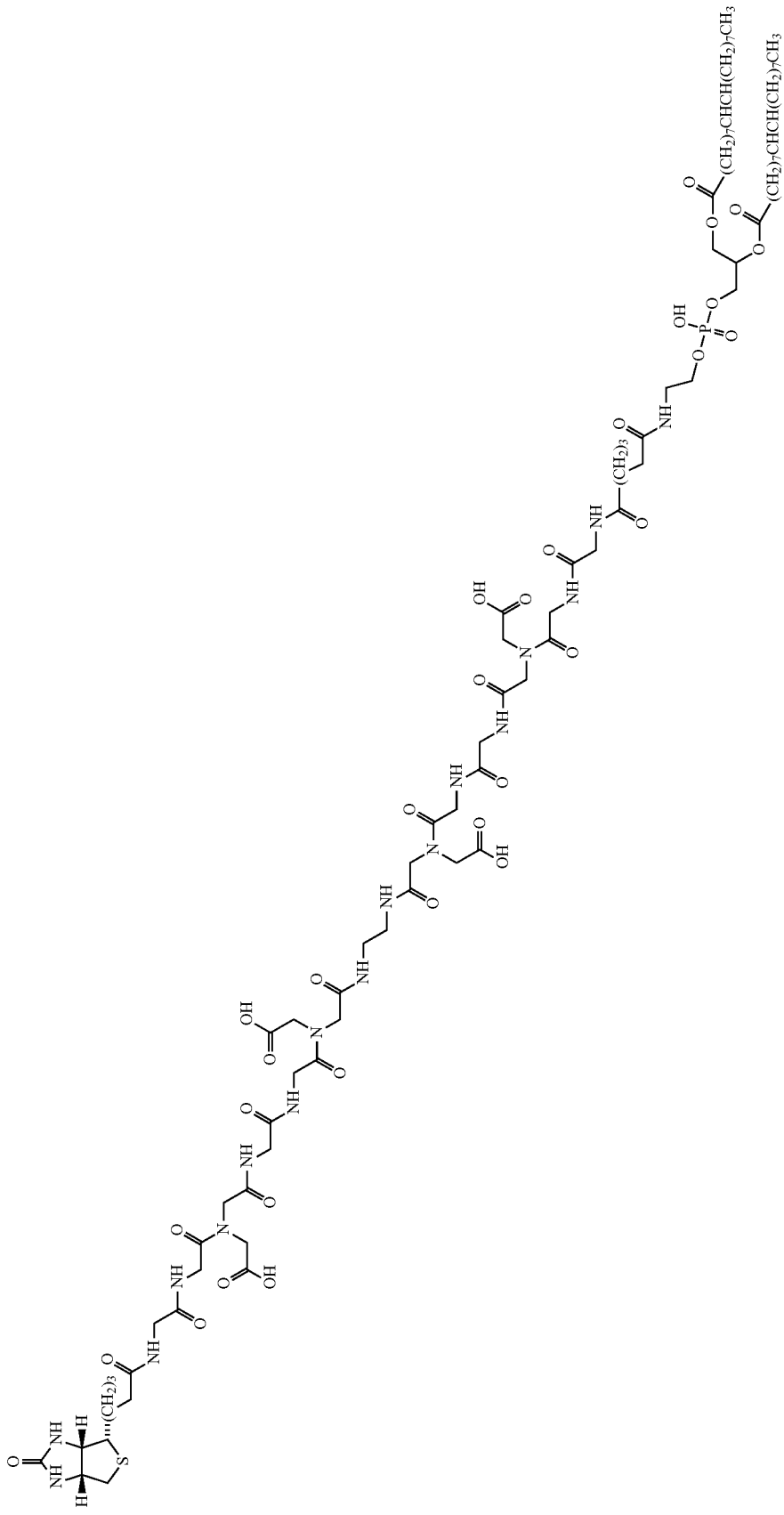
FSL-Biotin

Figure 13A:
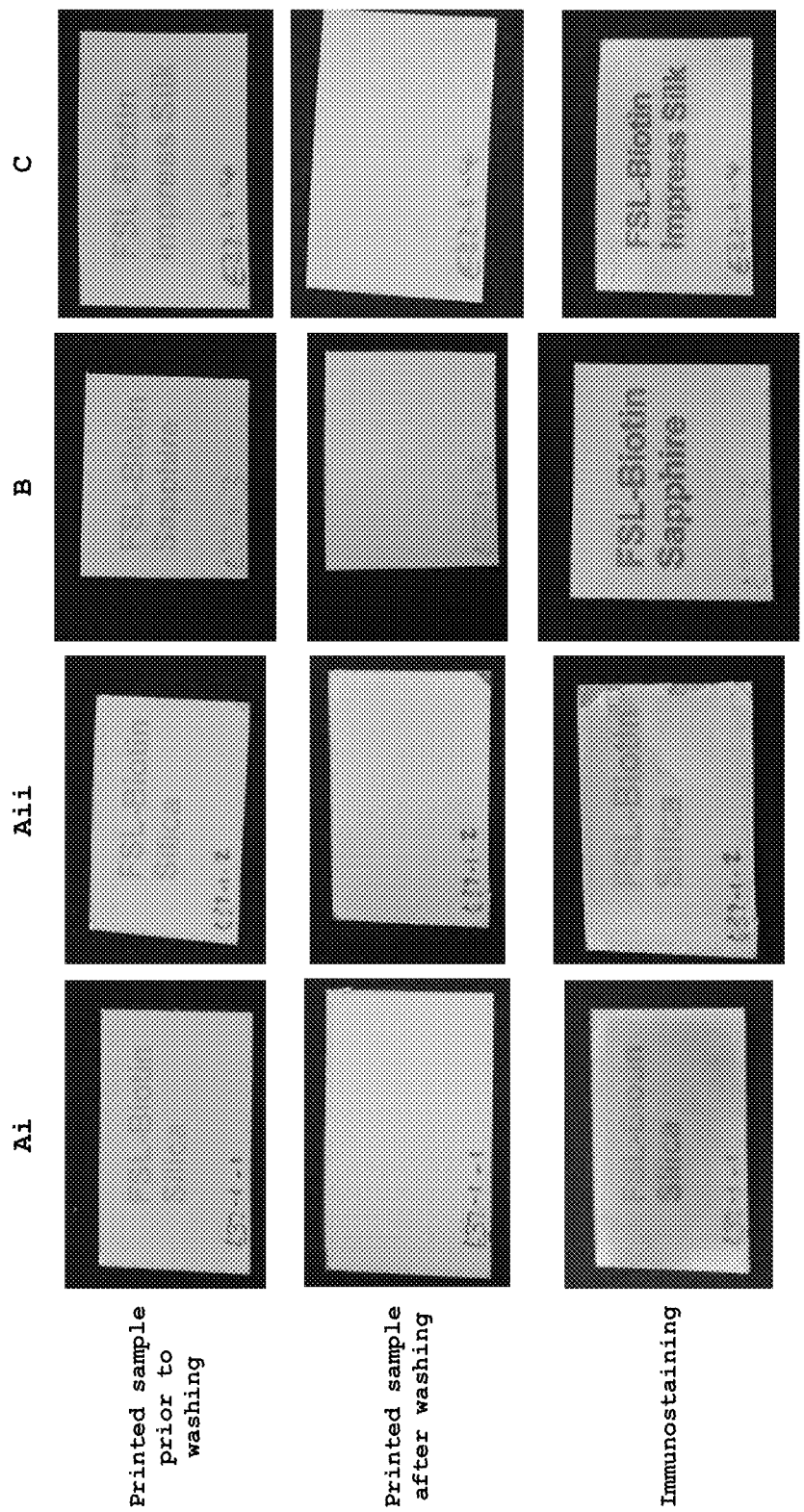

The samples of printed paper were placed in a beaker of deionised water for 15 minutes to remove the bromophenol blue dye and then air dried. The sample of aluminium backed silica gel TLC plate was immersed in a solution of 0.5% (w/v) polyisobutylmethacrylate in n-hexane and diethyl ether (PLEXIGUM P28) for one minute and then air dried. Neither the samples of printed paper nor sample of printed nitrocellulose was subjected to this treatment prior to immunostaining. For immunostaining the samples were first blocked by flooding the surface with a solution of 2% (w/v) BSA in PBS. The surface of each sample was then flooded with streptavidan-alkaline phosphatase conjugate (sigma) at a concentration of 2 µg/ml for 30 minutes at room temperature. The samples were then washed with PBS by flooding the surface of the membranes with PBS for 20 seconds and repeating 6 times with fresh PBS for each washing step. The printed samples were then washed with substrate buffer (100 mM Tris, 100 mM NaCl, 50 mM $MgCl_2$, pH 9.5) prior to flooding the surface of each sample with NBT/BCIP substrate (18.75 mg/ml nitro blue tetrazolium chloride and 9.4 mg/ml 5-bromo-4-chloro-3-indoyl-phosphate, toluidine salt in 67% (v/v) DMSO (Roche) diluted 50-fold in substrate buffer and incubated for 50 minutes at room temperature. The printed samples were rinsed with deionised water to stop the chromogenic reaction. The results of immunostaining each of the samples are presented in FIGS. 13A and 13B.

Printing on Other Substrates

Figure 14:
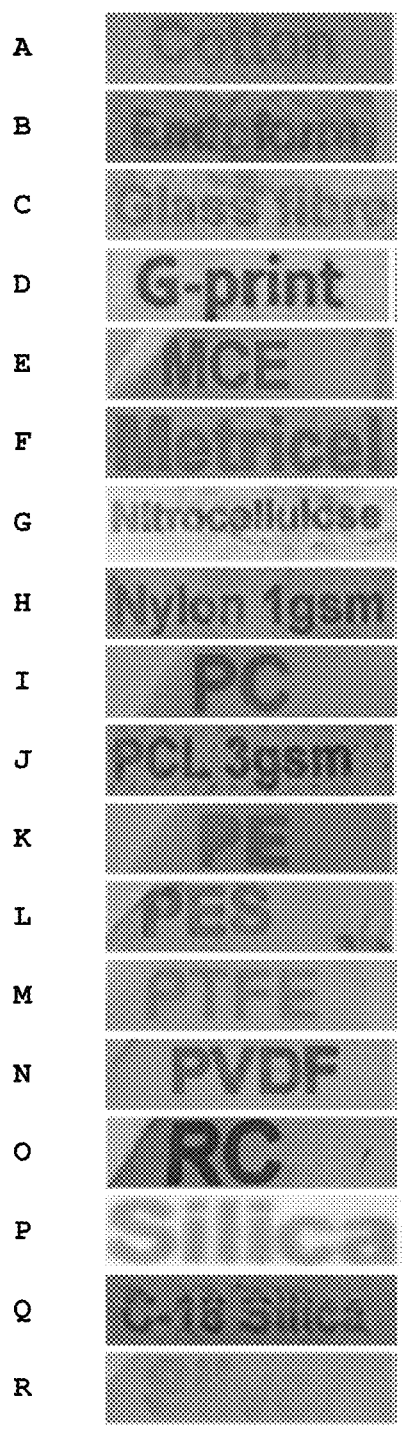
FIG. 14. Immunostaining with monoclonal antibody of the surface of substrates other than paper printed with a dispersion of FSL-A. The identity of the substrate employed is identified by the letters appearing following immunostaining (cotton fabric (A), collagen matrix (ovine) (B), glass borosilicate filter membrane (C), printer paper (D), mixed cellulose esters 0.45 µm filter membrane (E), cellulose triacetate filter membrane (F), nitrocellulose 0.45 µm membrane (G), polyamide PA66 electrospun nanofibres (H), polycarbonate 1 µm filter membrane, poly(ε-caprolactone) electrospun nanofibres (J), polyester 1 µm filter membrane (K), polyethersulfone 0.45 µm filter membrane (L), polytetrafluoroethylene 1 µm filter membrane (M), polyvinylidene fluoride 0.45 µm filter membrane (N), regenerated cellulose filter membrane (O), silica gel 60 Nano-Sil G TLC membrane (P), silica gel C18 RP-18W TLC membrane (Q) and silver 99.97% 3 µm filter membrane (R)).

The ability of substrates other than paper to be used in accordance with the method was demonstrated. The immune-stained samples of these printed substrates are presented in FIG. 14.

Localizing Cells to Discrete Areas on a Surface

Figure 15:
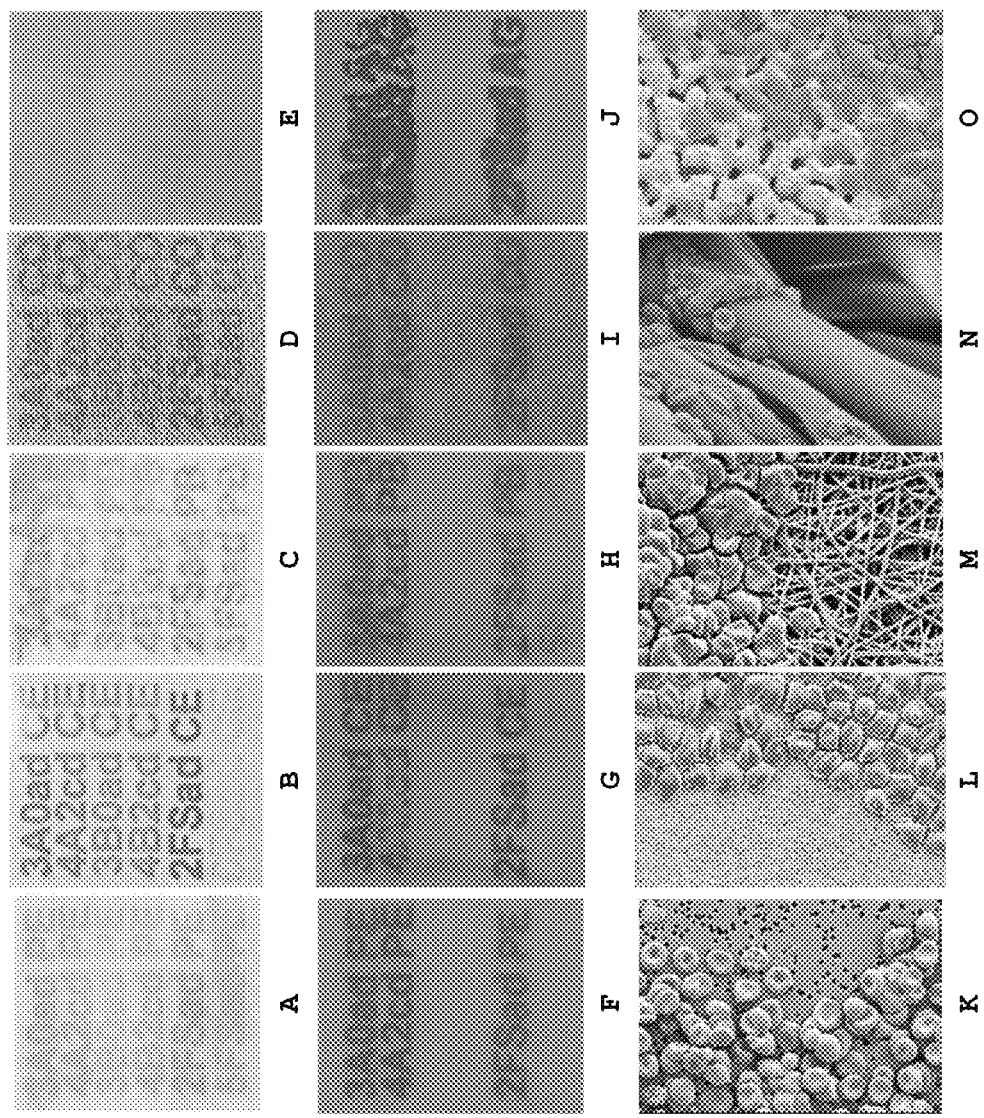
FIG. 15. Localisation of red blood cells to discrete areas on a surface. Synthetic constructs where the functional moiety was an epitope of a blood group antigen were printed o the surface. The upper row of images (A to E) show the location of the printed synthetic constructs as detected using the enzyme linked immunosorbent assays on surfaces and monoclonal antibodies cross-reactive with the A and B blood group antigens. The middle row of images (F to J) show blood type specific binding of these same surfaces when reacted with monoclonal IgM anti-A and used to capture blood group A red cells. The lower row of images (K to O) are scanning electron microscope (×2000) images of the edge of the printed areas, showing delineation between the printed and unprinted areas. The substrates are as identified in the images (PE—polyester 1 µm filter (A,F,K); CE—cellulose esters MG paper (B,G,L); PB—polyvinyl butyral nanofibres (C,H,M); CO—cotton fabric (D,I,N); AG—silver 99.97% 3 µm filter (E,J,O)).
Figure 16:
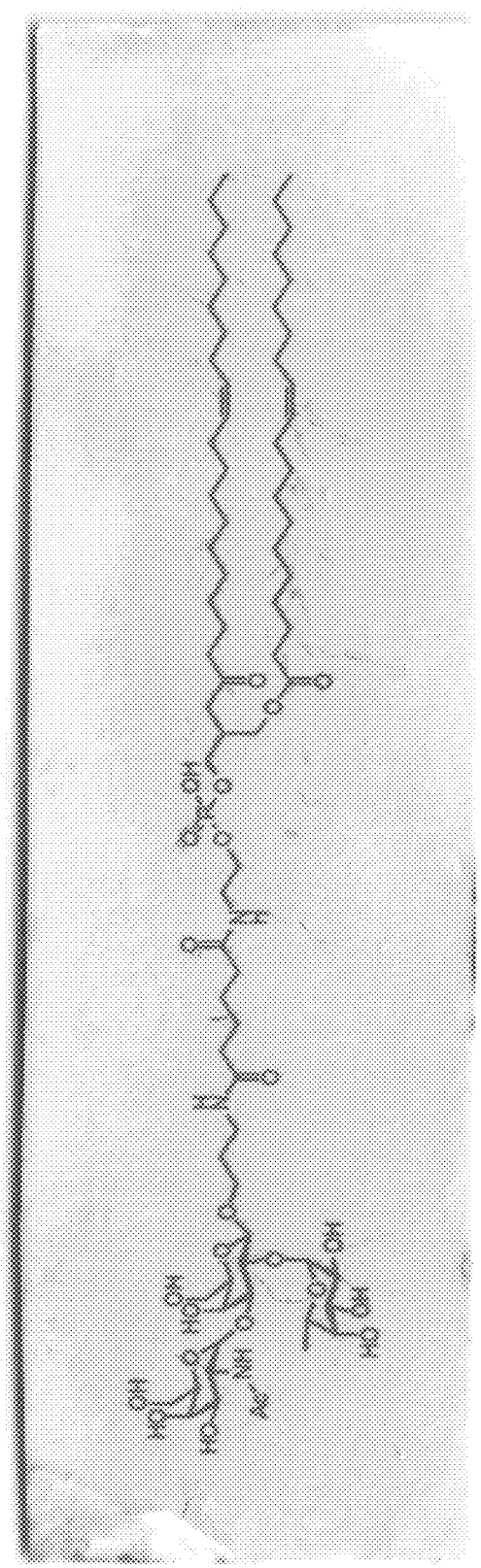
FIG. 16. The structure of the construct $A_{tri}$-sp-Ad-DOPE (I) (FSL-A) printed on paper using a dispersion of the construct according to the method of the invention.
Figure 17:
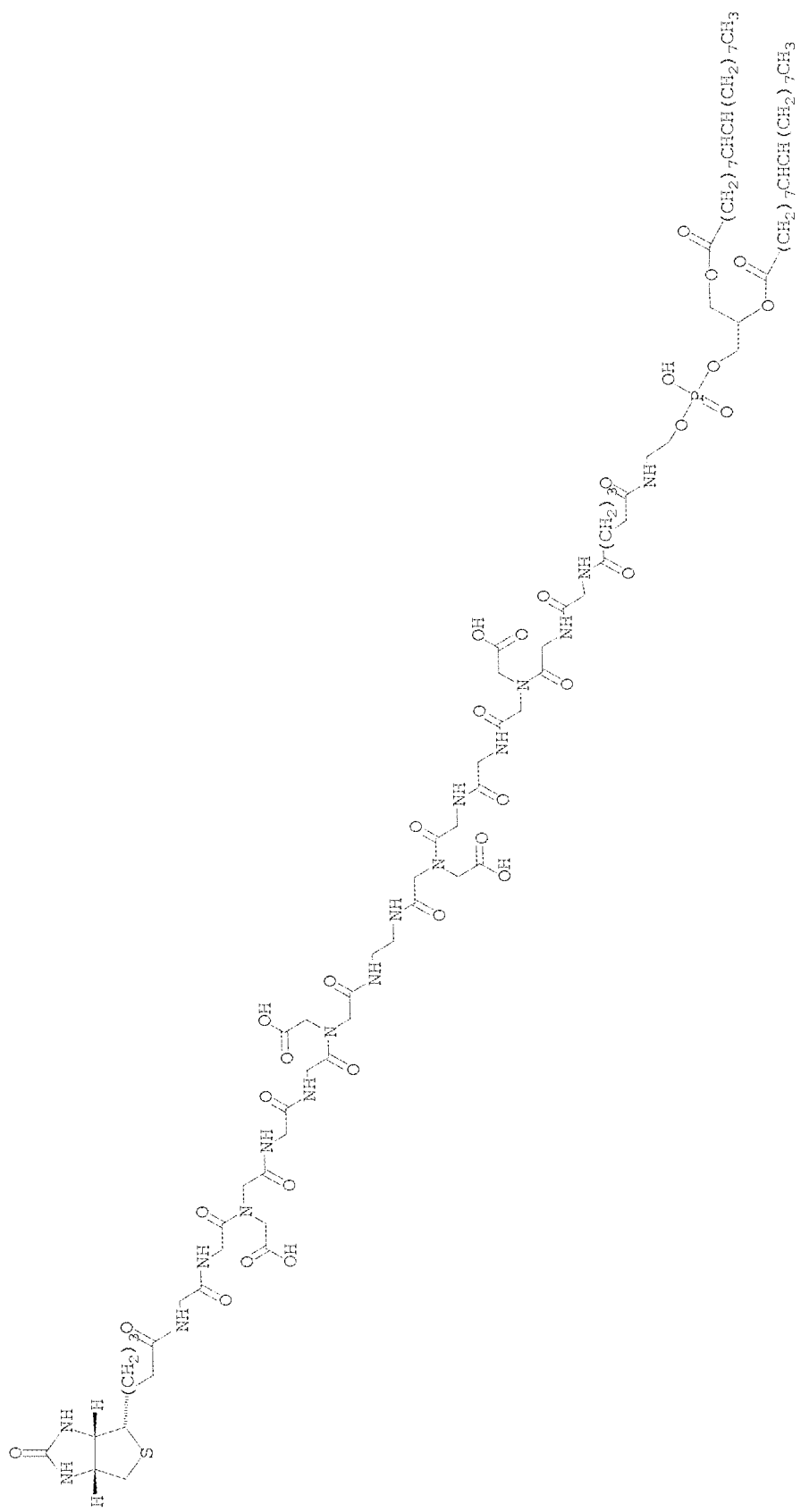
FIG. 17. The structure of the construct FSL-Biotin.

The printing of synthetic constructs can also be used to localize cells to discrete areas on a surface. Synthetic constructs where the functional moiety is an epitope (glycotope) of blood group antigens A or B are printed onto different surfaces using and inkjet printer. Following contacting the printed surfaces with anti-A antibody (IgM) the surfaces are contacted with a suspension of blood group A red blood cells. The red blood cells are observed to bind strongly and specifically to discrete areas on the surface where the antibody/synthetic construct complex is located as presented in FIG. 15.

Although the invention has been described by way of exemplary embodiments it should be appreciated that variations and modifications may be made without departing from the scope of the invention. Where known equivalents exist to specific features, such equivalents are incorporated as if specifically referred to in this specification.

REFERENCES

Barbulovic-Nad et al (2006) *Bio-microarray fabrication techniques*—A review Critical Reviews in Biotechnology, 26, 237-259.

Blixt et al (2004) *Printed covalent glycan array for ligand profiling of diverse glycan binding proteins* PNAS, 101 (49), 17033-17038.

Bovin and Huflejt (2008) *Unlimited glycochip* Trends Glycosci. Glycotechnol. 20(115), 245-258.

Campanero-Rhodes et al (2007) *N-glycolyl GM1 ganglioside as a receptor for simian virus 40* Journal of Virology, 81(23), 12846-12858.

Chai et al (2003) *Neoglycolipid technology: Deciphering information content of glycome* Methods in Enzymol., 362, 160-195.

Chai et al (2004) Products and methods U.S. patent application Ser. No. 10/855,072 (publ. no. US 2004/0259142 A1).

Chung-Yi et al (2009) *New development of glycan arrays* Org. Biomol. Chem., 7, 2247-2254.

Feizi (2006) *Oligosaccharide microarrays to decipher the glyco code* Abstracts of Papers, 231st ACS National Meeting, Atlanta, Ga., United States, Mar. 26-30, 2006, CARB-016 Publisher: American Chemical Society, Washington, D.C.

Feizi and Chai (2004) *Innovation: Oligosaccharide microarrays to decipher the glycocode* Nature Reviews Molecular Cell Biology, 5(7), 582-588.

Feizi et al (2003) *Neoglycolipids: identification of functional carbohydrate epitopes* Carbohydrate-Based Drug Discovery, Volume 2, 747-760. Editor(s): Wong, Chi-Huey. Publisher: Wiley-VCH Verlag GmbH & Co. KGaA, Weinheim, Germany.

Fukui (2003) *Carbohydrate microarray: a sweet spot for deciphering the information embedded in oligosaccharide structures* Seikagaku, 75(12), 1545-1550.

Fukui et al (2002) *Oligosaccharide microarrays for high-throughput detection and specificity assignments of carbohydrate-protein interactions* Nat. Biotechnol., 20(10), 1011-1017.

Huang et al (2006a) *Fabrication and application of neoglycolipid arrays in a microtitre plate* Bioorg. Med. Chem. Lett., 16, 2031-2033.

Huang et al (2006b) *Structure-function relations of carbohydrates by neoglycolipid arrays* Applied Biochemistry and Biotechnology, 133(3), 211-215.

Liu et al (2006) *Preparation of neoglycolipids with ring-closed cores via chemoselective oxime-ligation for microarray analysis of carbohydrate-protein interactions* Methods in Enzymol., 415(Glycobiology), 326-340.

Liu et al (2007) *Neoglycolipid Probes Prepared via Oxime Ligation for Micro-array Analysis of Oligosaccharide-Protein Interactions* Chemistry & Biology, 14(7), 847-859.

Palma et al (2006) *Ligands for the β-Glucan Receptor, Dectin-1, Assigned Using "Designer" Microarrays of Oligosaccharide Probes (Neoglycolipids) Generated from Glucan Polysaccharides* Journal of Biological Chemistry, 281(9), 5771-5779.

Shin et al (2005) *Carbohydrate microarrays: An advanced technology for functional studies of glycans* Chem. Eur. J., 11, 2894-2901.

Yamaguchi et al (2006) *Detection of oligosaccharide ligands for Hepatocyte growth factor/Scatter factor (HGF/SF), Keratinocyte growth factor (KGF/FGF-7), RANTES and Heparin cofactor II by neoglycolipid microarrays of glycosaminoglycan-derived oligosaccharide fragments* Glycoconjugate Journal, 23(7/8), 513-523.

The invention claimed is:

1. A method of localizing cells to at least one discrete area with a F-S-L synthetic construct on a surface comprising the steps of:
   selecting F as a functional moiety capable of associating with the cells by direct or indirect non-covalent interaction with biotin or an epitope of an antigen presented at the surface of the cells;
   selecting S as a spacer that provides the construct dispersible in water in the absence of organic solvents or detergents at a temperature of 25° C.;
   propelling droplets of a dispersion of the synthetic construct of structure F-S-L from a plurality of orifices located in a monolithic print head onto the at least one discrete area; and then
   contacting the surface with a suspension of the cells,
   where:
   L is a diacyl- or dialkyl-lipid.

2. The method of claim 1 where F is biotin, a glycan or a peptide.

3. The method of claim 2 where the concentration of the synthetic construct in the dispersion is 1 µM to 10 mM.

4. The method of claim 3 where L is a glycerophospholipid.

5. The method of claim 4 where L is a phosphatidylethanolamine.

6. The method of claim 5 where F is biotin.

7. The method of claim 6 where the cells are biotinylated and the contacting the surface with the suspension is preceded by contacting either the surface or the cells with an excess of avidin and washing.

8. The method of claim 6 where F—S is:

where:
  M is $CH_3$ or H;
  c is the integer 3, 4 or 5;
  d and e are independently the integer 1, 2 or 4; and
  $R_{13}$ is N of the primary amino of a diacyl or dialkyl-glycerophospholipid.

* * * * *

SEQUENCE LISTING

<160> NUMBER OF SEQ ID NOS: 35

<210> SEQ ID NO 1
<211> LENGTH: 26
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(7)
<223> OTHER INFORMATION: Optional proximal terminal sequence (PTS) of
      0 to 6 residues selected to promote solubility of the peptide.
      Xaa can be any amino acid.

<400> SEQUENCE: 1

Cys Xaa Xaa Xaa Xaa Xaa Xaa Trp Thr Pro Pro Arg Ala Gln Ile Thr
1               5                   10                  15

Gly Tyr Leu Thr Val Gly Leu Thr Arg Arg
            20                  25

<210> SEQ ID NO 2
<211> LENGTH: 27
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(7)
<223> OTHER INFORMATION: Optional proximal terminal sequence (PTS) of
      0 to 6 residues selected to promote solubility of the peptide.
      Xaa can be any amino acid.

<400> SEQUENCE: 2

Cys Xaa Xaa Xaa Xaa Xaa Xaa Trp Thr Pro Pro Arg Ala Gln Ile Thr
1               5                   10                  15

Gly Tyr Arg Leu Thr Val Gly Leu Thr Arg Arg
            20                  25

<210> SEQ ID NO 3
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (2)..(7)
<223> OTHER INFORMATION: Optional proximal terminal sequence (PTS) of
      0 to 6 residues selected to promote solubility of the peptide.
      Xaa can be any amino acid.

<400> SEQUENCE: 3

Cys Xaa Xaa Xaa Xaa Xaa Xaa Val Met Tyr Ala Ser Ser Gly
1               5                   10

<210> SEQ ID NO 4
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (8)..(13)
<223> OTHER INFORMATION: Optional proximal terminal sequence (PTS) of
      0 to 6 residues selected to promote solubility of the peptide.
      Xaa can be any amino acid.

```
<400> SEQUENCE: 4

Val Met Tyr Ala Ser Ser Gly Xaa Xaa Xaa Xaa Xaa Xaa Cys
1               5                  10

<210> SEQ ID NO 5
<211> LENGTH: 18
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (12)..(17)
<223> OTHER INFORMATION: Optional proximal terminal sequence (PTS) of
      0 to 6 residues selected to promote solubility of the peptide.
      Xaa can be any amino acid.

<400> SEQUENCE: 5

Asp Tyr His Arg Val Met Tyr Ala Ser Ser Gly Xaa Xaa Xaa Xaa
1               5                  10                  15

Xaa Cys

<210> SEQ ID NO 6
<211> LENGTH: 19
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (13)..(18)
<223> OTHER INFORMATION: Optional proximal terminal sequence (PTS) of
      0 to 6 residues selected to promote solubility of the peptide.
      Xaa can be any amino acid.

<400> SEQUENCE: 6

Thr Asn Gly Glu Thr Gly Gln Leu Val His Arg Phe Xaa Xaa Xaa Xaa
1               5                  10                  15

Xaa Xaa Cys

<210> SEQ ID NO 7
<211> LENGTH: 19
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (13)..(18)
<223> OTHER INFORMATION: Optional proximal terminal sequence (PTS) of
      0 to 6 residues selected to promote solubility of the peptide.
      Xaa can be any amino acid.

<400> SEQUENCE: 7

Thr Asn Gly Glu Met Gly Gln Leu Val His Arg Phe Xaa Xaa Xaa Xaa
1               5                  10                  15

Xaa Xaa Ala

<210> SEQ ID NO 8
<211> LENGTH: 20
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (14)..(19)
<223> OTHER INFORMATION: Optional proximal terminal sequence (PTS) of
```

```
      0 to 6 residues selected to promote solubility of the peptide.
      Xaa can be any amino acid.

<400> SEQUENCE: 8

Asp Thr Tyr Pro Ala His Thr Ala Asn Glu Val Ser Glu Xaa Xaa Xaa
1               5                   10                  15

Xaa Xaa Xaa Cys
            20

<210> SEQ ID NO 9
<211> LENGTH: 17
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (11)..(16)
<223> OTHER INFORMATION: Optional proximal terminal sequence (PTS) of
      0 to 6 residues selected to promote solubility of the peptide.
      Xaa can be any amino acid.

<400> SEQUENCE: 9

Thr Tyr Pro Ala His Thr Ala Asn Glu Val Xaa Xaa Xaa Xaa Xaa Xaa
1               5                   10                  15

Cys

<210> SEQ ID NO 10
<211> LENGTH: 15
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (9)..(14)
<223> OTHER INFORMATION: Optional proximal terminal sequence (PTS) of
      0 to 6 residues selected to promote solubility of the peptide.
      Xaa can be any amino acid.

<400> SEQUENCE: 10

Pro Ala His Thr Ala Asn Glu Val Xaa Xaa Xaa Xaa Xaa Xaa Cys
1               5                   10                  15

<210> SEQ ID NO 11
<211> LENGTH: 15
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (9)..(14)
<223> OTHER INFORMATION: Optional proximal terminal sequence (PTS) of
      0 to 6 residues selected to promote solubility of the peptide.
      Xaa can be any amino acid.

<400> SEQUENCE: 11

Tyr Pro Ala His Thr Ala Asn Glu Xaa Xaa Xaa Xaa Xaa Xaa Cys
1               5                   10                  15

<210> SEQ ID NO 12
<211> LENGTH: 15
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
```

```
<222> LOCATION: (9)..(14)
<223> OTHER INFORMATION: Optional proximal terminal sequence (PTS) of
      0 to 6 residues selected to promote solubility of the peptide.
      Xaa can be any amino acid.

<400> SEQUENCE: 12

Thr Tyr Pro Ala His Thr Ala Asn Xaa Xaa Xaa Xaa Xaa Xaa Cys
1               5                   10                  15

<210> SEQ ID NO 13
<211> LENGTH: 16
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (10)..(15)
<223> OTHER INFORMATION: Optional proximal terminal sequence (PTS) of
      0 to 6 residues selected to promote solubility of the peptide.
      Xaa can be any amino acid.

<400> SEQUENCE: 13

Thr Tyr Pro Ala His Thr Ala Asn Glu Xaa Xaa Xaa Xaa Xaa Xaa Cys
1               5                   10                  15

<210> SEQ ID NO 14
<211> LENGTH: 16
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (10)..(15)
<223> OTHER INFORMATION: Optional proximal terminal sequence (PTS) of
      0 to 6 residues selected to promote solubility of the peptide.
      Xaa can be any amino acid.

<400> SEQUENCE: 14

Tyr Pro Ala His Thr Ala Asn Glu Val Xaa Xaa Xaa Xaa Xaa Xaa Cys
1               5                   10                  15

<210> SEQ ID NO 15
<211> LENGTH: 16
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (10)..(15)
<223> OTHER INFORMATION: Optional proximal terminal sequence (PTS) of
      0 to 6 residues selected to promote solubility of the peptide.
      Xaa can be any amino acid.

<400> SEQUENCE: 15

Pro Ala His Thr Ala Asn Glu Val Ser Xaa Xaa Xaa Xaa Xaa Xaa Cys
1               5                   10                  15

<210> SEQ ID NO 16
<211> LENGTH: 17
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (11)..(16)
<223> OTHER INFORMATION: Optional proximal terminal sequence (PTS) of
      0 to 6 residues selected to promote solubility of the peptide.
```

Xaa can be any amino acid.

<400> SEQUENCE: 16

Asp Thr Tyr Pro Ala His Thr Ala Asn Glu Xaa Xaa Xaa Xaa Xaa Xaa
1               5                   10                  15

Cys

<210> SEQ ID NO 17
<211> LENGTH: 17
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (11)..(16)
<223> OTHER INFORMATION: Optional proximal terminal sequence (PTS) of
      0 to 6 residues selected to promote solubility of the peptide.
      Xaa can be any amino acid.

<400> SEQUENCE: 17

Tyr Pro Ala His Thr Ala Asn Glu Val Ser Xaa Xaa Xaa Xaa Xaa Xaa
1               5                   10                  15

Cys

<210> SEQ ID NO 18
<211> LENGTH: 17
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (11)..(16)
<223> OTHER INFORMATION: Optional proximal terminal sequence (PTS) of
      0 to 6 residues selected to promote solubility of the peptide.
      Xaa can be any amino acid.

<400> SEQUENCE: 18

Ser Gln Thr Asn Asp Lys His Lys Arg Asp Xaa Xaa Xaa Xaa Xaa Xaa
1               5                   10                  15

Cys

<210> SEQ ID NO 19
<211> LENGTH: 18
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (12)..(17)
<223> OTHER INFORMATION: Optional proximal terminal sequence (PTS) of
      0 to 6 residues selected to promote solubility of the peptide.
      Xaa can be any amino acid.

<400> SEQUENCE: 19

Gln Thr Asn Asp Lys His Lys Arg Asp Thr Tyr Xaa Xaa Xaa Xaa Xaa
1               5                   10                  15

Xaa Cys

<210> SEQ ID NO 20
<211> LENGTH: 31
<212> TYPE: PRT
<213> ORGANISM: Artificial sequence
<220> FEATURE:
<223> OTHER INFORMATION: Synthetic peptide

```
<220> FEATURE:
<221> NAME/KEY: MISC_FEATURE
<222> LOCATION: (25)..(30)
<223> OTHER INFORMATION: Optional proximal terminal sequence (PTS) of
      0 to 6 residues selected to promote solubility of the peptide.
      Xaa can be any amino acid.

<400> SEQUENCE: 20

Gln Thr Asn Asp Lys His Lys Arg Asp Thr Tyr Ser Ser Gln Thr Asn
1               5                   10                  15

Asp Met His Lys Arg Asp Thr Tyr Xaa Xaa Xaa Xaa Xaa Xaa Cys
            20                  25                  30

<210> SEQ ID NO 21
<211> LENGTH: 18
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (12)..(17)
<223> OTHER INFORMATION: Optional proximal terminal sequence (PTS) of
      0 to 6 residues selected to promote solubility of the peptide.
      Xaa can be any amino acid.

<400> SEQUENCE: 21

Gln Thr Asn Asp Met His Lys Arg Asp Thr Tyr Xaa Xaa Xaa Xaa Xaa
1               5                   10                  15

Xaa Cys

<210> SEQ ID NO 22
<211> LENGTH: 17
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (11)..(16)
<223> OTHER INFORMATION: Optional proximal terminal sequence (PTS) of
      0 to 6 residues selected to promote solubility of the peptide.
      Xaa can be any amino acid.

<400> SEQUENCE: 22

Ser Ser Gln Thr Asn Asp Lys His Lys Arg Xaa Xaa Xaa Xaa Xaa Xaa
1               5                   10                  15

Cys

<210> SEQ ID NO 23
<211> LENGTH: 20
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (14)..(19)
<223> OTHER INFORMATION: Optional proximal terminal sequence (PTS) of
      0 to 6 residues selected to promote solubility of the peptide.
      Xaa can be any amino acid.

<400> SEQUENCE: 23

Ser Ser Gln Thr Asn Asp Lys His Lys Arg Asp Thr Tyr Xaa Xaa Xaa
1               5                   10                  15

Xaa Xaa Xaa Cys
            20
```

<210> SEQ ID NO 24
<211> LENGTH: 20
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (14)..(19)
<223> OTHER INFORMATION: Optional proximal terminal sequence (PTS) of
      0 to 6 residues selected to promote solubility of the peptide.
      Xaa can be any amino acid.

<400> SEQUENCE: 24

Ser Ser Gln Thr Asn Asp Met His Lys Arg Asp Thr Tyr Xaa Xaa Xaa
1               5                   10                  15

Xaa Xaa Xaa Cys
            20

<210> SEQ ID NO 25
<211> LENGTH: 33
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (27)..(32)
<223> OTHER INFORMATION: Optional proximal terminal sequence (PTS) of
      0 to 6 residues selected to promote solubility of the peptide.
      Xaa can be any amino acid.

<400> SEQUENCE: 25

Ser Ser Gln Thr Asn Asp Lys His Lys Arg Asp Thr Tyr Ser Ser Gln
1               5                   10                  15

Thr Asn Asp Met His Lys Arg Asp Thr Tyr Xaa Xaa Xaa Xaa Xaa Xaa
                20                  25                  30

Cys

<210> SEQ ID NO 26
<211> LENGTH: 17
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (11)..(16)
<223> OTHER INFORMATION: Optional proximal terminal sequence (PTS) of
      0 to 6 residues selected to promote solubility of the peptide.
      Xaa can be any amino acid.

<400> SEQUENCE: 26

Gln Thr Asn Asp Lys His Lys Arg Asp Thr Xaa Xaa Xaa Xaa Xaa Xaa
1               5                   10                  15

Cys

<210> SEQ ID NO 27
<211> LENGTH: 18
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (12)..(17)
<223> OTHER INFORMATION: Optional proximal terminal sequence (PTS) of
      0 to 6 residues selected to promote solubility of the peptide.

Xaa can be any amino acid.

<400> SEQUENCE: 27

Ser Gln Thr Asn Asp Lys His Lys Arg Asp Thr Xaa Xaa Xaa Xaa Xaa
1               5                   10                  15

Xaa Cys

<210> SEQ ID NO 28
<211> LENGTH: 18
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (12)..(17)
<223> OTHER INFORMATION: Optional proximal terminal sequence (PTS) of
      0 to 6 residues selected to promote solubility of the peptide.
      Xaa can be any amino acid.

<400> SEQUENCE: 28

Thr Asn Asp Lys His Lys Arg Asp Thr Tyr Pro Xaa Xaa Xaa Xaa Xaa
1               5                   10                  15

Xaa Cys

<210> SEQ ID NO 29
<211> LENGTH: 17
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (11)..(16)
<223> OTHER INFORMATION: Optional proximal terminal sequence (PTS) of
      0 to 6 residues selected to promote solubility of the peptide.
      Xaa can be any amino acid.

<400> SEQUENCE: 29

Glu Glu Thr Gly Glu Thr Gly Gln Leu Val Xaa Xaa Xaa Xaa Xaa Xaa
1               5                   10                  15

Cys

<210> SEQ ID NO 30
<211> LENGTH: 17
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (11)..(16)
<223> OTHER INFORMATION: Optional proximal terminal sequence (PTS) of
      0 to 6 residues selected to promote solubility of the peptide.
      Xaa can be any amino acid.

<400> SEQUENCE: 30

Glu Glu Glu Thr Gly Glu Thr Gly Gln Leu Xaa Xaa Xaa Xaa Xaa Xaa
1               5                   10                  15

Cys

<210> SEQ ID NO 31
<211> LENGTH: 17
<212> TYPE: PRT
<213> ORGANISM: Artificial sequence
<220> FEATURE:
<223> OTHER INFORMATION: Synthetic peptide -continued

```
<220> FEATURE:
<221> NAME/KEY: MISC_FEATURE
<222> LOCATION: (11)..(16)
<223> OTHER INFORMATION: Optional proximal terminal sequence (PTS) of
      0 to 6 residues selected to promote solubility of the peptide.
      Xaa can be any amino acid.

<400> SEQUENCE: 31

Glu Thr Gly Glu Thr Gly Gln Leu Val His Xaa Xaa Xaa Xaa Xaa Xaa
1               5                   10                  15

Cys

<210> SEQ ID NO 32
<211> LENGTH: 16
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (10)..(15)
<223> OTHER INFORMATION: Optional proximal terminal sequence (PTS) of
      0 to 6 residues selected to promote solubility of the peptide.
      Xaa can be any amino acid.

<400> SEQUENCE: 32

Ser Pro Pro Arg Arg Ala Arg Val Thr Xaa Xaa Xaa Xaa Xaa Xaa Cys
1               5                   10                  15

<210> SEQ ID NO 33
<211> LENGTH: 23
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (17)..(22)
<223> OTHER INFORMATION: Optional proximal terminal sequence (PTS) of
      0 to 6 residues selected to promote solubility of the peptide.
      Xaa can be any amino acid.

<400> SEQUENCE: 33

Tyr Arg Tyr Arg Tyr Thr Pro Lys Glu Lys Thr Gly Pro Met Lys Glu
1               5                   10                  15

Xaa Xaa Xaa Xaa Xaa Xaa Cys
            20

<210> SEQ ID NO 34
<211> LENGTH: 15
<212> TYPE: PRT
<213> ORGANISM: Artificial sequence
<220> FEATURE:
<223> OTHER INFORMATION: Synthetic peptide
<220> FEATURE:
<221> NAME/KEY: MISC_FEATURE
<222> LOCATION: (9)..(14)
<223> OTHER INFORMATION: Optional proximal terminal sequence (PTS) of
      0 to 6 residues selected to promote solubility of the peptide.
      Xaa can be any amino acid.

<400> SEQUENCE: 34

Trp Gln Pro Pro Arg Ala Arg Ile Xaa Xaa Xaa Xaa Xaa Xaa Cys
1               5                   10                  15

<210> SEQ ID NO 35
<211> LENGTH: 17
<212> TYPE: PRT
<213> ORGANISM: Artificial sequence
```

```
<220> FEATURE:
<223> OTHER INFORMATION: Synthetic peptide
<220> FEATURE:
<221> NAME/KEY: MISC_FEATURE
<222> LOCATION: (11)..(16)
<223> OTHER INFORMATION: Optional proximal terminal sequence (PTS) of
      0 to 6 residues selected to promote solubility of the peptide.
      Xaa can be any amino acid.

<400> SEQUENCE: 35

Thr Ile Thr Gly Leu Glu Pro Gly Thr Glu Xaa Xaa Xaa Xaa Xaa Xaa
1               5                   10                  15

Cys
```